(12) United States Patent
Wang et al.

(10) Patent No.: US 10,526,608 B2
(45) Date of Patent: Jan. 7, 2020

(54) IN VITRO SELECTION OF FORMALDEHYDE CROSS-LINKING APTAMERS

(71) Applicant: The Governors of the University of Alberta, Edmonton (CA)

(72) Inventors: Zhixin Wang, Edmonton (CA); Hongquan Zhang, Ottawa (CA); Xing-Fang Li, Edmonton (CA); Xiaochun Le, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 15/797,782

(22) Filed: Oct. 30, 2017

(65) Prior Publication Data
US 2018/0119149 A1    May 3, 2018

Related U.S. Application Data

(60) Provisional application No. 62/414,910, filed on Oct. 31, 2016.

(51) Int. Cl.
| | |
|---|---|
| *C07H 21/04* | (2006.01) |
| *C12N 15/115* | (2010.01) |
| *G01N 33/53* | (2006.01) |
| *G01N 33/574* | (2006.01) |

(52) U.S. Cl.
CPC ....... *C12N 15/115* (2013.01); *G01N 33/5308* (2013.01); *G01N 33/57415* (2013.01); *C12N 2310/16* (2013.01); *C12N 2310/3517* (2013.01); *C12N 2320/10* (2013.01); *C12N 2330/31* (2013.01); *G01N 33/5748* (2013.01); *G01N 2333/82* (2013.01)

(58) Field of Classification Search
CPC ..................................................... C07H 21/04
See application file for complete search history.

(56) References Cited

U.S. PATENT DOCUMENTS

| | | | |
|---|---|---|---|
| 6,001,577 A | 12/1999 | Gold et al. | |
| 7,947,447 B2 | 5/2011 | Zichi et al. | |
| 2016/0003835 A1* | 1/2016 | Halbert ................ | C12N 15/115 506/9 |

OTHER PUBLICATIONS

Aquino-Jarquin et al., "RNA Aptamer Evolution: Two Decades of SELEction," International Journal of Molecular Sciences, 2011, vol. 12 (12), pp. 9155-9171.
Barker et al., "DNA-Protein Crosslinks: Their Induction, Repair, and Biological Consequences," Mutation Research, Mar. 2005, vol. 589 (2), pp. 111-135.
Berezovski et al., "Nonequilibrium Capillary Electrophoresis of Equilibrium Mixtures: A Universal Tool for Development of Aptamers," Journal of the American Chemical Society, Mar. 2005, vol. 127 (9), pp. 3165-3171.
Berezovski et al., "Non-SELEX Selection of Aptamers," Journal of the American Chemical Society, Feb. 2006, vol. 128 (5), pp. 1410-1411.
Berg et al., "Use of Formalin-Fixed and Paraffin-Embedded Tissues for Diagnosis and Therapy in Routine Clinical Settings," Methods in Molecular Biology, 2011, vol. 785, pp. 109-122.
Bock et al., "Photoaptamer Arrays Applied to Multiplexed Proteomic Analysis," Proteomics, Mar. 2004, vol. 4 (3), pp. 609-618.
Cho et al., "Quantitative Selection of DNA Aptamers through Microfluidic Selection and High-Throughput Sequencing," Proceedings of the National Academy of Sciences of the United States of America, Aug. 2010, vol. 107 (35), pp. 15373-15378.
Dahl et al., "MicroChIP—A Rapid Micro Chromatin Immunoprecipitation Assay for Small Cell Samples and Biopsies," Nucleic Acids Research, Feb. 2008, vol. 36 (3), p. e15.
Ellington et al., "In Vitro Selection of RNA Molecules that Bind Specific Ligands," Nature, Aug. 1990, vol. 346 (6287), pp. 818-822.
Gander et al., "Photoaptamer Chips for Clinical Diagnostics," Expert Review of Molecular Diagnostics, Jan. 2005, vol. 5 (1), pp. 1-3.
Gelinas et al., "Crystal Structure of Interleukin-6 in Complex with a Modified Nucleic Acid Ligand," Journal of Biological Chemistry, Mar. 2014, vol. 289 (12), pp. 8720-8734.
Gold et al., "Aptamer-Based Multiplexed Proteomic Technology for Biomarker Discovery," PloS one, Dec. 2010, vol. 5 (12), p. e15004.
Golden et al., "Diagnostic Potential of PhotoSELEX-Evolved ssDNA Aptamers," Journal of Biotechnology, Aug. 2000, vol. 81 (2-3), pp. 167-178.
Gopinath., "Methods Developed for SELEX," Analytical and Bioanalytical Chemistry, Jan. 2007, vol. 387 (1), pp. 171-182.
Green et al., "Inhibitory DNA Ligands to Platelet-Derived Growth Factor B-Chain," Biochemistry, Nov. 1996, vol. 35 (45), pp. 14413-14424.
Jackson., "Studies on Histone Organization in the Nucleosome Using Formaldehyde as a Reversible Cross-Linking Agent," Cell, Nov. 1978, vol. 15 (3), pp. 945-954.
Jensen et al., "Using in Vitro Selection to Direct the Covalent Attachment of Human Immunodeficiency Virus Type 1 Rev Protein to High-Affinity RNA Ligands," Proceedings of the National Academy of Sciences of the United States of America, Dec. 1995, vol. 92 (26), pp. 12220-12224.
Keefe et al., "Aptamers as Therapeutics," Nature Reviews Drug discovery, Jul. 2010, vol. 9 (7), pp. 537-550.
Kimoto et al., "Generation of High-Affinity DNA Aptamers Using an Expanded Genetic Alphabet," Nature Biotechnology, Apr. 2013, vol. 31 (5), pp. 453-457.
Klockenbusch et al., "Advancing Formaldehyde Cross-Linking Towards Quantitative Proteomic Applications," Analytical and Bioanalytical Chemistry, Sep. 2012, vol. 404 (4), pp. 1057-1067.
Kunkel et al., "Contact-Site Cross-Linking Agents," Molecular and Cellular Biochemistry, Jan. 1981, vol. 34 (1), pp. 3-13.
Li et al., "Aptamers Facilitating Amplified Detection of Biomolecules," Analytical Chemistry, Jan. 2015, vol. 87 (1), pp. 274-292.

(Continued)

*Primary Examiner* — Kimberly Chong
(74) *Attorney, Agent, or Firm* — Borden Ladner Cervais LLP

(57) ABSTRACT

The present disclosure relates generally to method of preparing aptamers, aptamers, and uses thereof.

13 Claims, 32 Drawing Sheets

Specification includes a Sequence Listing.

(56) References Cited

OTHER PUBLICATIONS

Liu et al., "DNase-Mediated Single-Cycle Selection of Aptamers for Proteins Blotted on a Membrane," Analytical Chemistry, Sep. 2012, vol. 84 (18), pp. 7603-7606.

Lou et al., "Micromagnetic Selection of Aptamers in Microfluidic Channels," Proceedings of the National Academy of Sciences of the United States of America, 2009, vol. 106 (9), pp. 2989-2994.

Lu et al., "Structural Characterization of Formaldehyde-Induced Cross-Links between Amino Acids and Deoxynucleosides and their Oligomers," Journal of the American Chemical Society, Mar. 2010, vol. 132 (10), pp. 3388-3399.

Ludwig et al., "Biomarkers in Cancer Staging, Prognosis and Treatment Selection," Nature Reviews Cancer, Nov. 2005, vol. 5 (11), pp. 845-856.

McGhee et al., "Formaldehyde as a Probe of DNA Structure. I. Reaction with Exocyclic Amino Groups of DNA Bases," Biochemistry, Mar. 1975, vol. 14 (6), pp. 1281-1296.

McGhee et al., "Formaldehyde as a Probe of DNA Structure. II. Reaction With Exocyclic imino Groups of DNA Bases," Biochemistry, Mar. 1975, vol. 14 (6), pp. 1297-1303.

Mendonsa et al., "In Vitro Evolution of Functional DNA Using Capillary Electrophoresis," Journal of the American Chemical Society, Jan. 2004, vol. 126 (1), pp. 20-21.

Metz et al., "Identification of Formaldehyde-Induced Modifications in Proteins: Reactions With Model Peptides," Journal of Biological Chemistry, Feb. 2004, vol. 279 (8), pp. 6235-6243.

Moasser., "Targeting the Function of the HER2 Oncogene in Human Cancer Therapeutics," Oncogene, Oct. 2007, vol. 26 (46), pp. 6577-6592.

Oh et al., "Improving Aptamer Selection Efficiency Through Volume Dilution, Magnetic Concentration, and Continuous Washing in Microfluidic Channels," Analytical Chemistry, Sep. 2011, vol. 83 (17), pp. 6883-6889.

Orlando., "Mapping Chromosomal Proteins in Vivo by Formaldehyde-Crosslinked-Chromatin Immunoprecipitation," Trends in Biochemical Sciences, Mar. 2000, vol. 25 (3), pp. 99-104.

Qin et al., "Exploring DNA-binding Proteins With in Vivo Chemical Cross-Linking and Mass Spectrometry," Journal of Proteome Research, Apr. 2009, vol. 8 (4), pp. 1983-1991.

Rubin et al., "The Basic Biology of HER2," Annals of Oncology: Official Journal of the European Society for Medical Oncology, 2001, vol. 12 Suppl 1, pp. S3-S8.

Schutze et al., "Probing the SELEX Process With Next-Generation Sequencing," PLoS One, Dec. 2011, vol. 6 (12), p. e29604.

Sefah et al., "In Vitro Selection With Artificial Expanded Genetic Information Systems," Proceedings of the National Academy of Sciences of the United States of America, Jan. 2014, vol. 111 (4), pp. 1449-1454.

Shoji et al., "Modified DNA Aptamer That Binds the (R)-Isomer of a Thalidomide Derivative With High Enantioselectivity," Journal of the American Chemical Society, Feb. 2007, vol. 129 (5), pp. 1456-1464.

Smith et al., "Sensitivity and Specificity of Photoaptamer Probes," Molecular & Cellular Proteomics, Jan. 2003, vol. 2 (1), pp. 11-18.

Solomon et al., "Formaldehyde-Mediated DNA-Protein Crosslinking: A Probe for in Vivo Chromatin Structures," Proceedings of the National Academy of Sciences of the United States of America, Oct. 1985, vol. 82 (19), pp. 6470-6474.

Sprung., "A Summary of the Reactions of Aldehydes with Amines," Chemical Reviews, Jun. 1940, vol. 26 (3), pp. 297-338.

Stoltenburg et al., "SELEX—A (r)evolutionary Method to Generate High-Affinity Nucleic Acid Ligands," Biomolecular Engineering, Oct. 2007, vol. 24 (4), pp. 381-403.

Sutherland et al., "Utility of Formaldehyde Cross-Linking and Mass Spectrometry in the Study of Protein-Protein Interactions," Journal of Mass Spectrometry, Jun. 2008, vol. 43 (6), pp. 699-715.

Tan et al., "Aptamers From Cell-Based Selection for Bioanalytical Applications," Chemical Reviews, Apr. 2013, vol. 113 (4), pp. 2842-2862.

Tebbutt et al., "Targeting the ERBB Family in Cancer: Couples Therapy," Nature Reviews Cancer, Sep. 2013, vol. 13 (9), pp. 663-673.

Tuerk et al., "Systematic Evolution of Ligands by Exponential Enrichment: RNA Ligands to Bacteriophage T4 DNA Polymerase," Science, Aug. 1990, vol. 249 (4968), pp. 505-510.

Van Simaeys et al., "Identification of Cell Membrane Protein Stress-induced Phosphoprotein 1 as a Potential Ovarian Cancer Biomarker Using Aptamers Selected by Cell Systematic Evolution of Ligands by Exponential Enrichment," Analytical Chemistry, May 2014, vol. 86 (9), pp. 4521-4527.

Vaught et al., "Expanding the Chemistry of DNA for in Vitro Selection," Journal of the American Chemical Society, Mar. 2010, vol. 132 (12), pp. 4141-4151.

Wiegand et al., "High-Affinity Oligonucleotide Ligands to Human IgE Inhibit Binding to Fc Epsilon Receptor I," Journal of Immunology, Jul. 1996, vol. 157 (1), pp. 221-230.

* cited by examiner

IN VITRO SELECTION OF
FORMALDEHYDE CROSS-LINKING
APTAMERS

CROSS REFERENCE TO RELATED APPLICATION

This application claims priority to U.S. Ser. No. 62/414,910, filed Oct. 31, 2016, the entire contents of which is hereby incorporated by reference in its entirety.

FIELD

The present disclosure relates generally to method of preparing aptamers, aptamers, and uses thereof.

BACKGROUND

Affinity probes, such as monoclonal antibodies, are one of the most powerful tools in the study of biology. Although the use of antibodies in bioanalytical assays has prevailed for over half a century, they do not fulfill the requirements needed for high-throughput profiling of the human proteome. Several synthetic affinity reagents, such as recombinant and engineered antibodies or nucleic acid aptamers, are generated through advancing bioengineering technologies. Among these new affinity reagents are aptamers: single stranded oligonucleotides whose structures that result from unique folding patterns allow them to bind to particular targets with high affinity.

However, affinity interaction alone is not always sufficient for the discovery of high-affinity aptamers and further the development of sensitive assays.

SUMMARY

In one aspect there is provided an aptamer comprising: a) a nucleic acid comprising any one of H1-H55 (SEQ ID NO: 1-53); b) a nucleic acid having at least 60% sequence identity to the nucleic acid sequence of a); c) a nucleic acid that hybridizes with the complementary strand of the nucleic acid of a); d) a nucleic acid that differs from a) by one or more nucleotides that are substituted, deleted, and/or inserted; or e) a derivative of a), b), c), or d); wherein said aptamer binds to HER2.

In one aspect there is provided an aptamer comprising: a) a nucleic acid comprising H12 (SEQ ID NO: 13); b) a nucleic acid having at least 70% sequence identity to the nucleic acid sequence of a);c) a nucleic acid that hybridizes with the complementary strand of the nucleic acid of a);d) a nucleic acid that differs from a) by one or more nucleotides that are substituted, deleted, and/or inserted; or e) a derivative of a), b), c), or d); wherein said aptamer binds to HER2.

In one aspect there is provided a method for detecting HER2 in a biological sample, comprising: contacting said sample with an aptamer of claim 1 or 2, to which a detectable label is bound and determining whether an increase in fluorescence occurs, wherein an increase in fluorescence is indicative of the presence of HER2 in the sample.

In one aspect, there is provided a method of characterizing a disease or disorder, comprising: a) contacting a biological sample with one or more aptamer of claim 1 or 2; b) detecting a presence or level of a complex between the one or more aptamer and the target bound by the one or more aptamer in the biological test sample formed in step (a); and (c) comparing the presence or level detected in step (b) to a reference level from a biological control sample, thereby characterizing the disease or disorder.

In one example, said target is HER2.

In one example, said disease or disorder is breast cancer.

In one example, said subject is a human.

In one aspect there is provided a kit for performing SELEX, comprising: formaldehyde and instructions for use with SELEX. In another example, the kit further comprises a ssDNA library.

In one example, further comprising one or more primers.

In one aspect there is provided a kit for detecting a biomarker in a sample, comprising: an aptamer of claim 1 or 2, and, optionally a control, and instructions for use.

In one aspect there is provided a method for producing a nucleic acid aptamer, comprising: (a) a complex formation step of mixing a single-stranded nucleic acid library with a target substance in a solution to form a complex of a single-stranded nucleic acid and the target substance; (b) a crosslinking step of mixing a crosslinking agent with the complex of a single-stranded nucleic acid and the target substance from step (a), (c) a recovery step of recovering the complex from the solution; (d) an amplification step of recovering the single-stranded nucleic acid from the complex and then amplifying the single-stranded nucleic acid by a nucleic acid amplification method; (e) and a single-stranded nucleic acid preparation step of converting the double-stranded nucleic acids obtained in the amplification step into single strands and then forming an intramolecular conformation.

In one example, the target substance is coated on a solid-phase support to immobilize the complex onto the solid-phase support.

In one example, the solid-phase support comprises a magnetic bead.

In one example, further comprising a repetitive step of repeating several times the round from the complex formation step to the single-stranded nucleic acid preparation step using the single-stranded nucleic acids obtained in the single-stranded nucleic acid preparation step as a new single-stranded nucleic acid library.

In one example, the repetitive step involves repeating 2 to 15 times the round from the complex formation step to the single-stranded nucleic acid preparation step.

In one example, the nucleic acid is a DNA.

In one example, the DNA comprises non-modified nucleotides.

In one example, the target is a peptide.

In one example, the peptide is human epidermal growth factor receptor 2 (ErbB2/HER2), human platelet-derived growth factor-BB (PDGF-BB), human immunoglobulin E (IgE), ubiquitin, cytotoxic T-lymphocyte-associated protein 4 (CTLA-4), or programmed death-ligand 1 (PD-L1).

In one example, the target is human epidermal growth factor receptor 2 (ErbB2/HER2) protein (HER2).

In one example, the cross-linking agent is formaldehyde or paraformaldehyde.

In one example, the cross-linking agent is a carbonyl, preferably an aldehyde, preferably an aldehyde that is water soluble.

In one example, the adehyde includes protected aldehydes, and aldehyde precursors (such as acetals, aminals, hemiaminals, urotropine, formaldehyde-releasing compounds)

In one example, the carbonyl includes aldehydes, ketones and keto esters with reactive carbonyl groups.

In one example, the cross-linking agent is an organic compound which contain at least one aldehyde group therein capable of reacting with amine groups which includes but are not limited to for example, formaldehyde, acetaldehyde, propionaldehyde, isobutyraldehyde, chloral, hydroxyethylaldehyde, hydroxypivalaldehyde, acrolein, crotonaldehyde, glycolaldehyde, glycoxylic acid, furfural, hydroxymethylfurfural, glucose, salicylaldehyde, hydroxyacetaldehyde, glyceraldehyde and the like, or polyaldehydes i.e. known organic compounds having more than one aldehyde group therein, such as glyoxal, methylglyoxal, glutaraldehyde, paraformaldehyde and the like, and all the commercial derivatives thereof sold in the form of various condensates.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1A:
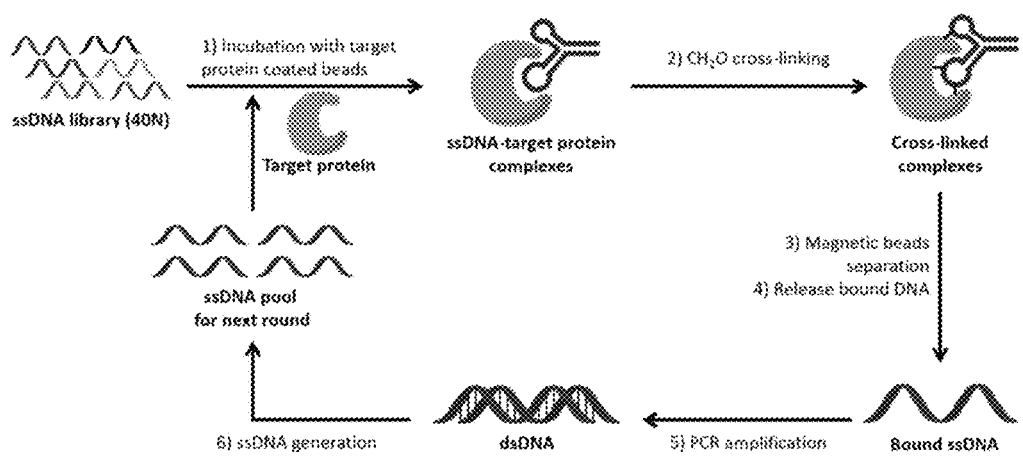
FIG. 1A Schematic of the SELEX process based on formaldehyde cross-linking. A random-sequence DNA library (2 nmole, ~$10^{15}$ sequences) was first incubated with the target protein that was coated on magnetic beads, allowing for the formation of protein-DNA complexes. Formaldehyde (1%, final concentration) was then added to generate cross-links between the protein and the bound DNA. After washing the magnetic beads with stringent conditions (urea buffer), the bound DNA was released by heating and amplified by polymerase chain reaction (PCR). The PCR products were used to prepare the ssDNA pool for the next round of selection.

In one aspect, there is described herein a method to stabilize aptamer-target complexes by using a crosslinking agent as an additional binding factor in conjunction with the in vitro selection technique termed Systematic Evolution of Ligands by EXponential enrichment (SELEX).

In some examples, in the SELEX process, a combinatory random library comprising single-stranded DNA (ssDNA) oligonucleotides is first produced. The oligonucleotides have an internal variable region having, for example, 40-60 nucleotides, which is flanked by primer regions on the 5' and 3' end. The primer regions serve as primer binding sites for a PCR amplification. Combinatory random libraries can be obtained from commercial suppliers. Starting from the single-stranded DNA oligonucleotide library, the oligonucleotides which bind best to the target are enriched via various selection and amplification steps in cycles.

Each cycle typically comprises the following part steps:
a) binding of the oligonucleotides to the target,
b) washing of the oligonucleotide-target complexes to remove non-bound oligonucleotides,
c) elution of the oligonucleotides bound to the target,
d) amplification of the eluted oligonucleotides by means of PCR,
e) purification of the relevant ssDNA oligonucleotides from the PCR product.

After each cycle the selected and enriched oligonucleotide pool is used as the starting material for the next cycle. For example, 8 to 12 cycles may be performed.

Stabilizing an aptamer-target with a crosslinking agent in SELEX

In one aspect described herein, a cross-linking agent is utilized as an additional binding factor in the interaction between aptamers and protein targets in SELEX. The formed complexes of target protein and DNA aptamer were "locked" by cross-linking after incubation, which converted the non-covalent interactions between protein and DNA into covalent bonds.

In one example, the crosslinking agent used is formaldehyde.

Formaldehyde is a highly reactive cross-linking reagent which can form covalent bonds between proteins, nucleic acids and other reactive molecules. Although the mechanism of formaldehyde cross-linking is complicated, the most accepted mechanism is that formaldehyde attacks the nucleophilic site, such as the amino and imino groups of amino acids (lysine, arginine, and histidine) and of DNA (dA, dC, dG), to form methylol intermediates or Schiff-bases by further dehydration. This intermediate can further react with another nucleophile and form the DNA-protein cross-links via methylene bridges. Formaldehyde can induced cross-links between amino acid Lys, Cys, His, and Trp with dG, dA, and dC.

This provides more cross-linking sites than photocross-linking without the need of any modification on protein and nucleic acid.

In one aspect described herein, a formaldehyde cross-linking was utilized as an additional binding factor in the interaction between aptamers and protein targets in SELEX. The formed complexes of target protein and DNA aptamer were "locked" by formaldehyde cross-linking after incubation, which converted the non-covalent interactions between protein and DNA into covalent bonds.

Stringent partition conditions were applied to remove the unbound and nonspecific binding DNA while minimizing the loss of any high affinity bound sequences.

In one example the crosslinking agent formaldehyde is used with the SELEX process.

In one example, the following process may be used:
a) binding of the oligonucleotides to the target,
b) generating cross-links between the target (e.g., a protein) and the aptamer from step a) with formaldehyde.
b) washing of the oligonucleotide-target complexes to remove non-bound oligonucleotides,
c) elution of the oligonucleotides bound to the target,
d) amplification of the eluted oligonucleotides by means of PCR,
e) purification of the relevant ssDNA oligonucleotides from the PCR product.

After each cycle the selected and enriched oligonucleotide pool is used as the starting material for the next cycle. For example, 3 to 12 cycles may be performed.

In a specific example, similar to the traditional SELEX process, a random-sequence DNA library is first incubated with the target protein which is coated on magnetic beads, allowing for the formation of non-covalent protein-DNA complexes. Formaldehyde is then added to generate cross-links between specific protein-DNA complexes. The formation of cross-links by formaldehyde turns dynamic, non-covalent interactions between protein and DNA into stable, covalent bonds. Stringent washing conditions can then be applied to eliminate the non-specific absorption of DNA on the solid matrix without interrupting the specific DNA binding. This accelerates the process of SELEX. After the removal of unbound DNA by washing, the bound DNA is released by heating. Formaldehyde cross-linking is fully reversible at high temperatures (>60° C.) in aqueous solutions. In a specific example, heating is carried out at about 95° C. for about 10 min. As shown herein, ssDNA can be released from complexes by heating which reverses the cross-linking and breaks the protein-aptamer complexes. Furthermore, the released DNA can be amplified directly by polymerase chain reaction (PCR) without interference by formaldehyde. Finally, the ssDNA pool was generated from the double-stranded PCR product for next round of selection.

In one example, the non-covalent affinity interaction between aptamer and target protein is converted to covalent bond by formaldehyde cross-linking, which reduces the dissociation of target-aptamer complexes. This improves the efficiency of SELEX when coupled with stringent partition condition.

In one example, through only three rounds of SELEX with formaldehyde cross-linking, high-affinity DNA aptamers with $K_d$s of nM range were selected for six different targets (e.g., human protein biomarkers), including human epidermal growth factor receptor 2 (ErbB2/HER2), human platelet-derived growth factor-BB (PDGF-BB), human immunoglobulin E (IgE), ubiquitin, cytotoxic T-lymphocyte-associated protein 4 (CTLA-4) and programmed death-ligand 1 (PD-L1).

In a specific example, the $K_d$ of HER2 aptamer H12 (GGCGCTTACA CGCAGGTTGA CTCAGACTAG ACTCTACAGC) (SEQ ID NO: 13) is as low as 6.4±2.7 nM.

Although formation of covalent complexes, the selectivity of aptamers against their targets does not affect by formaldehyde cross-linking. Aptamer H12 can specifically recognize overexpressed HER2 protein on the surface of SK-BR3 and MCF-7 cells as seen in live cell imaging.

In one example, there is provided a method for aptamer selection comprising reversible crosslinking of aptamer to a target, wherein the aptamer comprises non-modified nucleotides and the reversible crosslinking process does not result in a change of the chemical composition of either aptamer or target after crosslinking-reversal.

In some examples, an alternate and/or additional cross-linking agent is used. The alternate and/or additional cross-linking agent is selected to have properties corresponding to formaldehyde, for example a crosslinking agent with reversible crosslinking chemistry. In some examples, crosslinking agent is a compound that forms reversible crosslinks between amine groups.

In some examples, the crosslinking agent is a carbonyl compound, preferably an aldehyde, more preferably an aldehyde that is water soluble.

Aldehydes include protected aldehydes, and aldehyde precursors (such as acetals, aminals, hemiaminals, urotropine, formaldehyde-releasing compounds.

Preferred carbonyl compounds contemplated as cross-linkers according to the invention are aldehydes, ketones and keto esters with reactive carbonyl groups.

Specific examples are known organic compounds which contain at least one aldehyde group therein capable of reacting with amine groups which include but are not limited to for example, formaldehyde, acetaldehyde, propionaldehyde, isobutyraldehyde, chloral, hydroxyethylaldehyde, hydroxypivalaldehyde, acrolein, crotonaldehyde, glycolaldehyde, glycoxylic acid, furfural, hydroxymethylfurfural, glucose, salicylaldehyde, hydroxyacetaldehyde, glyceraldehyde and the like, or polyaldehydes i.e. known organic compounds having more than one aldehyde group therein, such as glyoxal, methylglyoxal, glutaraldehyde, paraformaldehyde and the like, and all the commercial derivatives thereof sold in the form of various condensates.

In preferred example, the aldehyde cross linkers are formaldehyde and paraformaldehyde.

In one aspect there is provided a method for producing a nucleic acid aptamer, comprising: (a) a complex formation step of mixing a single-stranded nucleic acid library with a target substance in a solution to form a complex of a single-stranded nucleic acid and the target substance; (b) a crosslinking step of mixing a crosslinking agent with the complex of a single-stranded nucleic acid and the target substance from step (a), (c) a recovery step of recovering the complex from the solution; (d) an amplification step of recovering the single-stranded nucleic acid from the complex and then amplifying the single-stranded nucleic acid by a nucleic acid amplification method; (e) and a single-stranded nucleic acid preparation step of converting the double-stranded nucleic acids obtained in the amplification step into single strands and then forming an intramolecular conformation.

In one example, the complex is recovered in step (c) using membrane filtration, gel electrophoresis, and the like. In another example, the complex is immobilized on a solid phase support.

In one example, the target substance is coated on a solid-phase support to immobilize the complex onto the solid-phase support.

In one example, the solid-phase support comprises a magnetic bead.

In one example, further comprising a repetitive step of repeating several times the round from the complex formation step to the single-stranded nucleic acid preparation step using the single-stranded nucleic acids obtained in the single-stranded nucleic acid preparation step as a new single-stranded nucleic acid library.

In one example, the repetitive step involves repeating 2 to 15 times the round from the complex formation step to the single-stranded nucleic acid preparation step.

In one example, the nucleic acid is a DNA. In another example, the DNA comprises non-modified nucleotides.

In one example, the target is a peptide.

In one example, the peptide is human epidermal growth factor receptor 2 (ErbB2/HER2), human platelet-derived growth factor-BB (PDGF-BB), human immunoglobulin E (IgE), ubiquitin, cytotoxic T-lymphocyte-associated protein 4 (CTLA-4), or programmed death-ligand 1 (PD-L1).

In a specific example, the target is human epidermal growth factor receptor 2 (ErbB2/HER2) protein (HER2).

In a specific example, the cross-lining agent is formaldehyde.

Aptamer

In one aspect, there is described herein an aptamer(s). The aptamer(s) may be obtained using the methods described herein. In one example, the aptamer(s) bind to a target.

The term "aptamer" as used herein refers to a single stranded nucleic acid molecule capable of specifically binding to a target.

The term "binds specifically" refers to high avidity and/or high affinity binding of an aptamer to a target (e.g., HER2 protein). Aptamers which bind specifically to a target of interest may be capable of binding other polypeptides at weak, yet detectable, level. Such weak binding, or background binding, is readily discernable from the specific aptamer binding to the compound or polypeptide of interest, e.g., by use of appropriate controls, as would be known to the worker skilled in the art.

The aptamer-target binding takes place, for example, via the structure compatibility, so-called "stacking interactions" in aromatic ring structures (stacking forces by electron interaction with adjacent bases), electrostatic interactions (e.g. van der Waals, ionic, dipole forces) and hydrogen bridge bonds.

The nucleic acid molecule may be a natural nucleic acid such as a DNA, an RNA, or a combination thereof. Also, the nucleic acid may partially or wholly comprise a non-natural nucleotide or a non-natural nucleic acid.

In a specific example, the nucleic acid is a DNA. Thus, in one example the aptamer is a DNA aptamer.

The term "DNA aptamer" as used herein refers to an aptamer consisting of deoxyribonucleotides.

Aptamers generally comprise between 5 and 120 nucleotides and can be selected in vitro according to the processes described herein, such as using SELEX with a crosslinking agent. In a specific example, the crosslinking agent is formaldehyde.

The term "target" as used herein refers to a substance that can serve as a target to which the nucleic acid aptamer binds.

A target can be any appropriate entity that can be detected when recognized by an aptamer, for example a biomaterial to which the nucleic acid aptamer can bind. In one example, the target comprises a protein or polypeptide. As used herein, "protein," "polypeptide" and "peptide" are used interchangeably unless stated otherwise. The target can be a nucleic acid, including DNA, RNA, and various subspecies of any thereof as disclosed herein or known in the art. The target can comprise a lipid. The target can comprise a carbohydrate. The target can comprise a low molecular-weight compound. The target can also be a complex, e.g., a complex comprising protein, nucleic acids, lipids and/or carbohydrates.

The target may be selected according to the intended use.

In one example, the target is a peptide, more preferably a polypeptide (e.g. a protein).

The term "protein" as used herein corresponds to an amino acid polymer. This includes the proteins, protein fragments, genetically modified proteins, oligopeptides and analogs thereof. The target protein may include a protein of therapeutic interest.

In a specific example, the target is a biomarker.

In one example, the biomarker is a biomarker protein.

Typically, a purified target is used. Preferably, the target is not contaminated (or is minimally contaminated) by impurities. In some example, polypeptide used as the target substance may be a fusion polypeptide comprising a tag sequence fused therewith.

In one example the target is human epidermal growth factor receptor 2 (ErbB2/HER2), human platelet-derived growth factor-BB (PDGF-BB), human immunoglobulin E (IgE), ubiquitin, cytotoxic T-lymphocyte-associated protein 4 (CTLA-4), or programmed death-ligand 1 (PD-L1).

In a specific example, the target is human epidermal growth factor receptor 2 (ErbB2/HER2) protein (HER2).

In one example, in which the target is human epidermal growth factor receptor 2 (ErbB2/HER2) protein, the aptamers in Table 1 ("HER2 aptamers") were identified using the methods described herein.

TABLE 1

HER2 aptamers

| ID | Sequence (5' to 3') | SEQ ID NO: |
|---|---|---|
| H1 | TGCCCCTAGG CGTGGCTGCA GCGTCTAATT GTGTTTATGA | 1 |
| H2 | ATTGGGTCTA TGGGTTGAAT CATTTCGGAC GTTTTACGTA | 2 |
| H3 | CGACATGTGC TGCGTGTACG ACTGTGTGCT CTATCTCGAG | 3 |
| H4 | CTACGCAACA ATCATAGGTG ATACCGGGCT GTTGTACAAT | 4 |
| H5 | GTAGGGATCG CTAGAAGGGT CAAAGTTAGG TCATGTAGGG | 5 |
| H6 | AACCGTAGGT GAAACGGAAG TCCCGGTTGG GGATCAATAT | 6 |
| H7 | AACCTTAGTA GGTACTCATG ACGTGGTCCA AGCCTTGTTT | 7 |
| H8 | GAGGGGGGGC CGCTACTGAG CACTCAAAGA CGCAATGCCC | 8 |
| H9 | GTGTGCAGCA ACGAGACTCA GCGACTAGCC CGTACGCCTG | 9 |
| H11, H16, H43 | TGGAGTGATT GCTCTAGTAG GGTTTCATGG GGCCCGATCC | 10, 11, 12 |
| H12, H13, H14, H15, H19, H25, H36, H37, H38, H41, H44 | GGCGCTTACA CGCAGGTTGA CTCAGACTAG ACTCTACAGC | 13, 14, 15, 16, 17, 18, 19, 20, 21, 22, 23 |
| H17, H18 | GATTGGCAGT TAGCGTTTTT CTGAGCATTC GAAGGTTATA | 24, 25 |
| H20, H24, H39, H45 | GAATCCTTCA CTGGTGGGTT CTGTTTCGGC TTTTTAAAAT | 26, 27, 28, 29 |
| H21, H40, H42 | CATGCGGTAC CGGTGAAACT AGAACGAATT TAAAGGCGAC | 30, 31, 32 |
| H22, H23 | CCTTAGGCTA GGGCAATTTC AACTCGCTTG ACGTCGAATA | 33, 34 |
| H26 | TTGAGTCATT ACCGTAAGTA CATCAACTAC TTAGTTAGTC | 35 |
| H28 | AGTCAGGGTG AAGAACCCGT GTCACCGGTC ATTTTCTAAT | 36 |
| H29 | GTCGAGAGTA TAATATTTCC GCTTAAACTA GTGTGTCGCC | 37 |
| H30 | TGTCAGCTAA CGTGGGTTTG TTACCGTGG CTTAGTTAGC | 38 |
| H31 | ACCATGAACA GCTGGCATTC CATGGATCTA ACGCGGAATT | 39 |
| H32 | CAATTGGCGC GGGGATTCCG CACCCTGAA TGTTCAGGGC | 40 |
| H33 | TGGGAAGTGT TACAATTCTG GTAGGGGTGT GGATTTAGGG | 41 |

TABLE 1-continued

HER2 aptamers

| ID | Sequence (5' to 3') | SEQ ID NO: |
|---|---|---|
| H34 | GGGCACGCAT AGCAAGGCGT ATATGAAGCG TCAGTTTTCC | 42 |
| H35 | GGAGTTATCC ATTCGCACAT AACTGCATTC ATCCGCTTAG | 43 |
| H46 | TAGTCTGATG CGATATACTC GGCGGTCGGG GGGGTAGGTT | 44 |
| H47 | GGAGTTTTAA GCGTTTGTGG CGAGATAACC TGGTTGTGCA | 45 |
| H48 | CCCAGATGAG GAATGAGGGC CTCACGTAGG GTGTGCAGCC | 46 |
| H49 | GCAAGACATA ACGTATAATC ATGGCGATAC CCTGCTTCCG | 47 |
| H50 | AACTGAGTCC ATGCTACTAG CAGCCTGAGG TGGATACTCT | 48 |
| H51 | GGGTATGATT TTGGACCCGA GTAGGCTATT TTAATTCAAA | 49 |
| H52 | CAGAACTGTG ACATGGCTTG GCCCATGACT TAAAGGAGTG | 50 |
| H53 | CATATGAACG TTTCTACAAT TTTAACGAGA CAGTTTTGCG | 51 |
| H54 | ACAATTGAGG CTATCAGTTC TGCTAGAAGT TGACTGGATC | 52 |
| H55 | TCTCTACCTG ATGTATAATT TACGTCACTA AGTCCCGCCG | 53 |

Thus, in one example, the HER2 aptamer is an aptamer comprising or consisting of the nucleic acid sequence selected from one or more of the aptamers H1-H55 (SEQ NO: 1-53).

In a specific example, the HER2 aptamer an aptamer comprising or consisting of the nucleic acid sequence H12 (SEQ ID NO: 13).

In some examples, a HER2 aptamer is a truncated aptamer comprising or consisting of the nucleic acid sequence selected from one or more of the aptamers H1-H55, having less than 40 bases. In some examples, the truncated aptamer comprises or consists of 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, or 5 bases, selected from one or more of the aptamers H1-H55.

In one example, the aptamer comprises or consists of 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, or 5 bases, of H12 (GGCGCTTACA CGCAGGTTGA CTCAGACTAG ACTCTACAGC) (SEQ ID NO: 13).

In another example, a HER2 aptamer is a "fragment" of the aptamers of Table

A "fragment" of the aptamer sequence may comprise a subsequence that binds to the same target as the full length sequence.

In one example, the HER2 aptamer comprises or consists of a fragment from one or more of the aptamers H1-H55 (SEQ ID NO: 1 -53).

In one example, the HER 2 aptamer comprises or consists of a fragment of the aptamer H12 (GGCGCTTACA CGCAGGTTGA CTCAGACTAG ACTCTACAGC) (SEQ ID NO: 13).

In one example, a HER2 aptamer is a derivative of one or more of the aptamers of Table 1.

The term "derivative" as used herein refers to an aptamer which has a chemical structure which does not occur in natural DNA or RNA.

The nucleotide sequences of aptamers identified using the methods described herein, or disclosed in Table 1, can be modified.

In some examples, the aptamer contains one or more chemical modifications. As used herein in a polynucleotide such as an aptamers identified using the methods described herein, or the aptamers in Table 1, the terms "chemical modification" or, as appropriate, "chemically modified" refer to modification with respect to adenosine (A), guanosine (G), uridine (U), thymidine (T) or cytidine (C) ribo- or deoxyribnucleosides in one or more of their position, pattern, percent or population.

The modifications may be various distinct modifications. In some embodiments, the regions may contain one, two, or more (optionally different) nucleoside or nucleotide modifications. In some embodiments, a modified polynucleotide, introduced to a cell may exhibit reduced degradation in the cell, as compared to an unmodified polynucleotide.

In some examples, there is provided an aptamer which is derived from an aptamer having one of the sequences of H1-H55 (SEQ ID NO: 1 to 53) such that in one of the sequences of SEQ H1 to H55 (SEQ ID NO: 1 to 53) one or more nucleotides are substituted, removed (deleted), added within the sequence (inserted) and/or added at the 5' end and/or 3' end, wherein such an aptamer binds to HER2

In one example, the aptamer is H12 (GGCGCTTACA CGCAGGTTGA CTCAGACTAG ACTCTACAGC) (SEQ ID NO: 13) which contains one or more chemical modification.

In some examples, the aptamer is an isolated polynucleotide having a nucleotide sequence that is at least 60% identical to the nucleotide sequence identified by the methods herein or in Table 1. In some examples, the isolated nucleic acid molecule is at least 65%, 70%, 75%, 80%, 85%, 90%, 91%, 92%, 93%, 94%, 95%, 96%, 97%, 98%, 99% or more, identical to the nucleotide sequence identified by the methods herein or in Table 1. In the case of an isolated polynucleotide which is longer than or equivalent in length to the reference sequence, e.g., a sequence identified by the methods herein and in Table 1, the comparison is made with the full length of the reference sequence. Where the isolated polynucleotide is shorter than the reference sequence, e.g., shorter than a sequence identified by the methods above, the comparison is made to a segment of the reference sequence of the same length (excluding any loop required by the homology calculation).

The term "sequence identity" as used herein, refers to the extent that sequences are identical on a nucleotide-by-nucleotide basis over a window of comparison. Thus, a "percentage of sequence identity" may be calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity.

In one example, the aptamer is an isolated aptamer which is at least 65%, 70%, 75%, 80%, 85%, 90%, 91%, 92%, 93%, 94%, 95%, 96%, 97%, 98%, 99% or more, identical to H12 (GGCGCTTACA CGCAGGTTGA CTCAGACTAG ACTCTACAGC), In some examples, there is provided an aptamer is an aptamer that hybridizes with a nucleotide sequence identified by the methods herein or in Table 1, or to their complementary strand, under stringency conditions described below.

As used herein, the term "hybridizes under low stringency, medium stringency, or high stringency" describes conditions for hybridization and washing. Aqueous and non-aqueous methods can be used.

In one example, low stringency conditions include but are not limited to from at least about 1% v/v to at least about 15% v/v formaldehyde and from at least about 1 M to at least about 2 M salt for hybridization at 42° C., and at least about 1 M to at least about 2 M salt for washing at 42° C.

In one example, medium stringency conditions include but are not limited to from at least about 16% v/v to at least about 30% v/v formaldehyde and from at least about 0.5 M to at least about 0.9 M salt for hybridization at 42° C., and at least about 0.1 M to at least about 0.2 M salt for washing at 55° C.

In one example, high stringency conditions include and encompass from at least about 31% v/v to at least about 50% v/v formaldehyde and from about 0.01 M to about 0.15 M salt for hybridization at 42° C., and about 0.01 M to about 0.02 M salt for washing at 55° C.

Other stringency conditions are well known in the art and a skilled artisan will recognize that various factors can be manipulated to optimize the specificity of the hybridization. Optimization of the stringency of the final washes can serve to ensure a high degree of hybridization.

While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the Tm for formation of a DNA-DNA hybrid. It is well known in the art that the Tm is the melting temperature, or temperature at which two complementary polynucleotide sequences dissociate. Methods for estimating Tm are well known in the art.

Biomarker Detection

An aptamer identified using the methods described herein, or the aptamers of Table 1, or as described herein, may be used to provide in vitro or in vivo detection or imaging, to provide a diagnostic readout (e.g., prognosis, diagnosis, therapeutic monitoring, or theranostic).

The term "prognosis" as used herein refers to the prediction of the likelihood of cancer-attributable death or progression, including recurrence, metastatic spread, and drug resistance, of a neoplastic disease, such as breast cancer.

The term "prognostic marker" as used herein refers to a marker that informs about the outcome of a patient in the absence of systemic therapy or portends an outcome different from that of the patients without the marker, despite empiric (not targeted to the marker) systemic therapy.

The term "predictive marker" as used herein refers to a marker that predicts that differential efficacy (benefit) of a particular therapy based on marker status.

The term "diagnosis" as used herein, refers to the identification of a molecular and/or pathological state, disease or condition, such as the identification of breast cancer, or other type of cancer.

The term "therapeutic monitoring" as used herein refers to the observation of the response of the subject to the treatment administered to it.

Thus, in another aspect, there is described a method for biomarker detection using an aptamer. In one example, there is described a method for biomarker detection in a subject. In another example, there is described a method for biomarker detection in a sample from a subject.

The term "biomarker" refers, in the most general sense, to a biological metric of the condition of a cell or patient health or disease status. A non-limiting listing of general biomarkers includes biologically derived molecules found in a mammal, cell surface markers, differential expression of, for example, a protein, protein truncations, phosphorylations, dephosphorylations, ubiquitination, de-ubiquitination, metabolites, hormones at any stage of biosynthesis, cytokines, chemokines, and combinations thereof. A subset of biomarkers are used for diagnostic and therapeutic selection purposes to help pathologists diagnose disease and to help doctors prescribe therapy.

In one example, the subject has cancer or is suspected of having cancer.

The term "cancer" as used herein, refers to or describes the physiological condition in a mammal that is typically characterized by unregulated cell growth. Examples of cancer include but are not limited to, breast cancer. Additional examples include, but are not limited to ovarian cancer, lung cancer, lymphoma, leukemia, germ cell cancer and primary of unknown origin (PRUNK).

In one example, the subject has breast cancer or is suspected of having breast cancer.

As used herein, "breast cancer" refers to a cancer that starts in a tissue of the breast, such a ductal carcinoma or lobular carcinoma and includes both early stage and late stage breast cancer. Breast cancer may be invasive or non-invasive and/or comprise malignant epithelial cells. Optionally, breast cancer may be classified according to molecular subtypes such as estrogen receptor (ER) and/or Her2 positive or negative as known in the art. In another embodiment, "breast cancer" refers to a cancer that starts in a non-adjacent tissue but which later metastasizes to the breast.

As used herein, "metastasis" refers to the spread of breast cancer from the breast to a non-adjacent part, tissue or organ of the test subject. In one embodiment, metastasis includes "lymph node metastasis" and/or "distant metastasis." As used herein, "lymph node metastasis" refers to the spread of cancer to the lymph system of a test subject. For example, lymph node metastasis includes the presence of malignant cells in one or more lymph nodes of a test subject, such as in the lymph nodes that are proximal to the breast cancer, for example in one or more sentinel lymph nodes. "Distant metastasis" refers to metastasis that is present in another non-adjacent part, tissue or organ of a test subject such as in lung, liver, brain or bone or in a distal lymph node.

The term "subject" or "patient" as used herein, refers to any mammal or non-mammal that would benefit from determining the benefit from treatment, treatment, diagnosis, therapeutic monitoring and/or prognosis. In certain examples a subject or patient includes, but is not limited to, humans, farm animals, companion animals (such as cats, dogs and horses), primates and rodent (such as mice and rats). In a specific embodiment, the subject is a human. In an additional specific embodiment, the subject is female. In another example the subject is male.

In one example, the biomarker is human epidermal growth factor receptor 2 (ErbB2/HER2), human platelet-derived growth factor-BB (PDGF-BB), human immunoglobulin E (IgE), ubiquitin, cytotoxic T-lymphocyte-associated protein 4 (CTLA-4) and programmed death-ligand 1 (PD-L1).

In a specific example, the biomarker is HER2 protein.

In some example, the aptamers herein are used to assess biomarker status.

The term "biomarker status" refers to assessment of a biomarker(s) in a patient, or patient's cells, and typically is reported as "biomarker positive" when the biomarker is present or "biomarker negative" when the biomarker is absent. When a protein receptor is used as a biomarker (e.g. HER2), a biomarker positive result is also referred to as the receptor being over-expressed or amplified and a biomarker negative result is referred to as the receptor being normally expressed or non- amplified.

For diseases where a biomarker or biomarker signature is a prognostic indicator of disease progression or predicts therapeutic efficacy, current clinical practice relies on the measurement of the amount of biomarker or its related mutations to refine a patient's diagnosis by classifying the patient as either biomarker negative or positive. Determination of biomarker status is often used to guide selection of the drug therapeutic to treat a patient. The cut-off value of a biomarker measurement that is used to distinguish biomarker positive and biomarker negative patients varies from biomarker to biomarker. When the biomarker is a drug target, the cut-off value is the condition above which a patient will receive a therapeutic that targets the biomarker and below which a patient will not receive a therapeutic that targets the biomarker.

The term "HER2 status" refers to assessment of expression of HER2 in a patient, or patient's cells (e.g., cancer cells) as a biomarker, and the status typically is reported as "HER2 positive" when the biomarker is present in overabundance as compared to a normal healthy non-cancer breast tissue sample or "HER2 negative" when the biomarker is present at a level no greater than a normal healthy non-cancer breast tissue sample as determined by an immunohistochemistry (IHC) stain test of a fixed tissue sample.

In some examples, the aptamers H1-H55 (SEQ ID NO: 1 to 53), or the aptamers described herein, are used to measure and/or detect the biomarker HER2.

In a specific example, the aptamer H12 (SEQ ID NO: 13) is used to measure and/or detect the biomarker HER2 in a sample from a subject.

In some examples, the aptamers H1-H55 (SEQ ID NO: 1 to 53), or the aptamers described herein, are used to measure and/or detect the HER2 status in a sample from a subject.

In a specific example, the aptamer H12 (SEQ ID NO: 13) is used to measure and/or detect the HER2 status in a sample from a subject.

In one example, a method of the present application comprises qualitatively or quantitatively determining, analyzing or measuring a biological sample from a subject for the presence or absence, or amount or concentration, of HER2 protein.

In some examples, a patient sample is compared to a control sample.

A suitable control can be used wherein the amount of predictive marker in the control sample is indicative of the amount of predictive marker in a subject that does not have cancer.

In one example, in determining whether there is high (e.g., strong) or low (e.g., weak or absent) amount of the biomarker, the patient sample may be compared to one or more control samples. In one example, a control sample has had known and/or established level of the predictive maker tumour staining. In one example, a control sample is a patient sample that has known and/or established levels of predictive marker tumour staining and/or known clinical outcome. In one example, a control is a cell line that has a known amount of predictive maker staining.

In some example, a control is not used and qualitative or quantitative methods are used to determine the presence or absence, or amount or concentration of the protein of interest.

In a specific example, one or more of the HER2 aptamers H1-H55 (SEQ ID NO: 1 to 53), or the aptamers described herein, are used to measure and/or detect the HER2 status in a sample from a subject.

In a specific example, the HER2 aptamer H12 (SEQ ID NO: 13) is used to measure and/or detect the HER2 status in a sample from a subject.

In a specific example, aptamers specifically and selectively bind to a protein of interest, for example the protein HER2.

When the aptamer is brought into contact with the target, an aptamer-target complex forms by binding of the aptamer to the target. The binding or the binding event can be detected, for example, visually, optically, photonically, electronically, acoustically, opto-acoustically, according to weight and/or mass, electrochemically, electrooptically, spectrometrically, enzymatically or otherwise chemically, biochemically or physically.

In one example, in the case of a labeling-free detection, the aptamer is fixed, for example, on to a surface and the change in the layer thickness after adding on of the target is determined using one of the methods mentioned, such as e.g. via a change in the optical properties of the sensor layer (e.g. refractive index). A further method for labeling-free detection is measurement of the change in weight after binding of the aptamer to the target using a microbalance, or measurement of a change in frequency of vibrating quartz after binding of the aptamer to the target, which is provided on the surface of the vibrating quartz.

Complexes may be detected directly or indirectly.

In cases where the complexing is not directly detectable, the complex can be rendered visible by labeling, for example in an indicator reaction after direct or indirect coupling of a complexing partner with a labeling substance. Either the aptamer used or the target can be provided with a labeling (label). In some examples, the aptamer is labeled.

In some example, the aptamers also comprise a label. The term "label" as used herein is an identifiable substance that is detectable in an assay and that can be attached to a molecule creating a labeled molecule. The behavior of the labeled molecule can then be monitored and/or studied and/or detected.

Examples of labels include, but are not limited to, various enzymes, prosthetic groups, fluorescent materials, luminescent materials, bioluminescent materials, radioactive materials, positron emitting nuclides, including metals, using various positron emission tomographies, and nonradioactive paramagnetic metal ions. The detectable substance may be coupled or conjugated either directly to the aptamer (or fragment thereof) or indirectly, through an intermediate. The particular label used will depend upon the type of assay.

A wide variety of detectable moieties can be used, with the choice of label depending on the sensitivity required, ease of conjugation, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

In some examples, detection can be carried out by means of radioactive isotopes with which the aptamer is labeled, preferably $^3$H, $_{14}$C, $^{32}$P, $^{33}$P, $^{35}$S or $^{125}$I. In scintillation counting, the radioactive radiation emitted by the radioactively labeled aptamer-target complex is measured indirectly. A scintillator substance is excited by the radioactive radiation. During the transition into the base state, the excitation energy is released again as flashes of light, which are amplified by a photoelectron multiplier (photomultiplier) and counted.

In one example, a sample containing cancerous cells or suspected as containing cancerous cells is obtained from the breast cancer patient. Collection of such a sample is well known to the skilled worker. In a specific example, the sample is a breast tissue sample. Methods of obtaining a breast tissue sample, processing and/or storage of such a sample are also well known to the skilled worker.

Breast tissues sample may be fresh-frozen and/or formalin-fixed, paraffin-embedded tissue blocks prepared for study by immunohistochemistry (IHC). In one example, the sample is a formalin fixed and/or paraffin-embedded tumor tissue from a biopsy or surgical resection of a cancer (e.g., tumor).

The methods of the present invention may be accomplished using any suitable method or system of immunohistochemistry using one or more of the aptamers using the methods described herein, the aptamers of table 1, and the aptamers as described herein. Non limiting examples include automated systems, quantitative IHC, semi-quantitative IHC, and manual methods.

The term "quantitative" immunohistochemistry refers to an automated method of scanning and scoring samples that have undergone immunohistochemistry, to identify and quantitate the presence of a specified biomarker, such as an antigen or other protein. For example, to quantitate HER2. The score given to the sample is a numerical representation of the intensity of the immunohistochemical staining of the sample, and represents the amount of target biomarker present in the sample. As used herein, Optical Density (OD) is a numerical score that represents intensity of staining as well as the percentage of cells that are stained. As used herein, semi-quantitative immunohistochemistry refers to scoring of immunohistochemical results by human eye, where a trained operator ranks results numerically (e.g., as 0, 1 or 2).

Automated sample processing, scanning and analysis systems suitable for use with immunohistochemistry are known in the art, and may be used with the present invention. Such systems may include automated staining and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light microscopes with digital image processing systems to perform quantitative analysis on cells and tissues, including immunostained samples.

In a specific example, the detection, analysis or measurement of Bad protein within a breast tissue sample is carried out using immunohistochemistry (IHC). It will be clear to the skilled worker that other immuno assays, both qualitative or quantitative, may be used in the present invention.

In a specific example, the detection, analysis or measurement of Bik protein within a breast tissue sample is carried out using immunohistochemistry (IHC). It will be clear to the skilled worker that other immuno assays, both qualitative or quantitative, may be used in the present invention.

In one example, immunohistochemisty is carried out using tissue microarrays from formalin fixed breast tissues using a TMArrayer™.

Other examples that may be used in the detection, analysis or measurement of Bad include, but are not limited to, immunoprecipitation and mass spectrometry.

Additional examples that may be used in the detection of HER2 include, but are not limited to, quantitative fluorescence activated cell sorting, enzyme linked immunosorbent assay, immunohistochemistry, quantitative immunohistochemistry, fluorescence resonance energy transfer, Forster resonance energy transfer, biomolecular fluorescence complementation, mass spectrometry, immunoblot assay and coimmunoprecipitation assay.

The term "treatment" as used herein, refers to clinical intervention in an attempt to alter the course of the subject or cell being treated. In non-limiting examples, treatment includes preventing or delaying recurrence of disease, alleviation of symptoms, diminishment of any direct or indirect pathological consequences of the disease, preventing metastasis, decreasing the rate of disease progression, amelioration or palliation of the disease state, and remission or improved prognosis.

Kits

Method of the invention are conveniently practiced by providing the compounds and/or compositions used in such method in the form of a kit. Such kit preferably contains the composition. Such a kit preferably contains instructions for the use thereof.

In one example, there is described a kit for performing SELEX, comprising: formaldehyde and instructions for use with SELEX. In another example, the kit further comprises a ssDNA library. In another example, the kit further comprises one or more primers.

In one example, there is described a kit for detecting a biomarker in a sample, comprising: an aptamer as described herein, and instructions for use.

The kit may include instructions for use in detecting breast cancer, determining risk of metastasis, determining tumor grade, and determining tumor sub-type. In a specific example, the kit may be useful in predicting metastatic potential of a breast cancer tumor.

To gain a better understanding of the invention described herein, the following examples are set forth. It should be understood that these examples are for illustrative purposes only. Therefore, they should not limit the scope of this invention in anyway.

EXAMPLES

Materials and Methods
Materials

Recombinant human platelet-derived growth factor-BB (PDGF-BB), human epidermal growth factor receptor 2 (ErbB2/HER2) and PE-conjugated mouse anti-human ErbB2/HER2 monoclonal antibody were purchased from R&D Systems (Minneapolis, Minn.). Human immunoglobulin E (IgE) was obtained from Athens Research & Technology (Athens, Ga.). Dynabeads® M-270 Carboxylic Acid and MyOne Streptavidin C1 magnetic beads, N-hydroxyl succinimide ester (NHS), 1-ethyl-3-(3-dimethylaminopropyl)carbodiimide hydrochloride (EDC) and cell culture reagents were ordered from Invitrogen (Burlington, ON). All DNA oligonucleotides including the initial DNA library and forward and reverse primers were obtained from Integrated DNA Technologies (Coralville, IA).

Immobilization of Target Protein on Magnetic Beads

Magnetic beads coated with carboxylic acid groups (Dynabeads® M-270 carboxylic acid, Invitrogen Dynal) were conjugated with target proteins for selection, following the manufacture's protocol. The magnetic beads were initially washed twice with 2-(N-morpholino) ethane sulfonic acid (MES) buffer (25 mM, pH 5.0). The magnetic beads were then activated by EDC (50 mg/mL) and NHS (50 mg/mL) in MES buffer at room temperature for 30 min on slow tilt rotation. After activation with EDC and NHS, the magnetic beads were washed 4 times with MES buffer. The target proteins were mixed with the activated magnetic beads at the ratio of 5 μg protein per mg beads and incubated at room temperature for 2 h on slow rotation. After conjugation, the unbound proteins in supernatant were removed by a magnet separator. The protein-coated magnetic beads were then incubated in Tris-HCl buffer (50 mM pH 7.4) at room temperature for 15 min to quench the non-reacted activated carboxylic acid group. Finally, the protein-coated magnetic beads were washed 4 times with PBS buffer containing 0.1% HSA and stored at 4° C. in the same buffer.

Cross-Linking Selection of Aptamer by Using Formaldehyde

The initial ssDNA random library for selection consisted of a 40-base random region flanked by two 20-base primer binding sequences: 5'-AGCAG CACAG AGGTC AGATG-[40N]-CCTAT GCGTG CTACC GTGAA-3' (SEQ ID NO: 54). The sequences of oligonucleotides used in this work are listed in Table 2.

TABLE 2

Sequences of ssDNA library and primers used in this study.

| | Sequence (5' to 3') | SEQ ID NO: |
|---|---|---|
| Library | AGCAG CACAG AGGTC AGATG-[40N]-CCTAT GCGTG CTACC GTGAA | 54 |
| Forward primer | AGCAG CACAG AGGTC AGATG | 55 |
| Reverse primer | TTCAC GGTAG CACGC ATAGG | 56 |
| FAM-labeled forward primer | [FAM]-AGCAG CACAG AGGTC AGATG | 57 |
| Biotin-labeled reverse primer | [Biotin]-TTCAC GGTAG CACGC ATAGG | 58 |

The initial ssDNA library was denatured by heating at 95° C. for 10 min, chilled on ice for 10 min, and then placed at room temperature for another 10 min before use. The target protein-coated magnetic beads were washed twice with HEPES binding buffer (40 mM HEPES pH 7.5, 125 mM NaCl, 5 mM KCl, 5 mM $MgCl_2$, 1 mM CaCl, 0.05% Tween20). The ssDNA library (2 nmol, about $10^{15}$ molecules) was mixed with protein-conjugated magnetic beads (about 108 beads) in 100 μL HEPES binding buffer. In order to reduce the non-specific absorption, herring sperm DNA (0.02% of final concentration) and HSA protein (0.05% of final concentration) were also added into the mixture. The mixture was incubated at 37° C. for 30 min with gentle rotation, allowing for the formation of protein-DNA complexes. After incubation, formaldehyde (1% of final concentration) was added into the mixture to cross-link at room temperature for 30 min. The unbound DNA was then removed by washing 5 times with urea wash buffer (8M urea, 0.05% Triton X-100). The magnetic beads were diluted with 1 mL urea wash buffer and stood for 30 min at 37° C. between wash steps. After washing with urea wash buffer, magnetic beads were resuspended in 100 μL of Tris-HCl buffer (10 mM, pH 8.0). Then, the bound DNA was released and eluted from the target protein-coated magnetic beads by heating at 95° C. for 10 min. These conditions can both denature the protein and reverse the cross-links. The eluted DNA was amplified by PCR to generate a new ssDNA pool for the next round of selection. In each subsequent round, counter selection was performed by incubating the DNA pool from the previous round with HSA-coated magnetic beads, then transferring the supernatant to the target protein-coated magnetic beads for selection. After three rounds of formaldehyde cross-linking selection, the binding affinity of ssDNA pool from each round of selection was determined by a magnetic bead-based fluorescence assay. The final ssDNA pool of the third round was cloned for sequencing.

PCR Amplification and ssDNA Generation

The released ssDNA in the supernatant was collected by magnet separation for PCR amplification. The PCR mixture was prepared with 10 μL of the released ssDNA as the template DNA in the total volume of 50 μL. The mixture also included 1× PCR reaction buffer, 0.2 mM dNTP, 2.8 mM MgCl2, 1 μM forward primer with FAM labeling, 1 pM reverse primer with biotin labeling, 5% DMSO and 1.25 U platinum Taq DNA polymerase. The PCR mixture was preheated at 94° C. for 10 min, followed by 24 thermal cycles of heating at 94° C. for 30 s, annealing at 57° C. for 30 s, and extending at 72° C. for 30 s and finished with a final extension step at 72° C. for 10 min.

Pilot PCR was performed first to determine the optimal number of PCR amplification cycles, which is the number of cycles without unwanted longer or shorter PCR by-products. An aliquot of PCR mixture (5 μL) was taken out during the extension step at 3, 6, 9, 12, 15, 18, 21 and 24 cycles and stored on ice until the end of PCR thermocycling. Then, the optimal PCR cycle number was determined by using a 8% native polyacrylamide gel (PAGE) to separate the aliquots of the PCR mixture at different cycles.

The remaining released DNA (90 μL) was amplified via preparative PCR with the same conditions as in the pilot PCR at the optimal cycle number by using FAM-labeled forward primer and biotin-labeled reverse primer. The biotin-labeled dsDNA products after PCR amplification were captured on Dynabeads MyOne Streptavidin C1 (Invitrogen Dynal) magnetic beads and removed from the other components of the PCR mixture by following the manufacture's protocol. The "sense" strands used as thessDNA pool for the next round of selection, were generated by de-hybridizing the double-stranded PCR product with NaOH solution (20 mM) at 37° C. for 5 min. The supernatant was collected by magnet separation and neutralized with HCl solution (80 mM). The concentration of the ssDNA pool was estimated via UV-vis absorption at the wavelength of 260 nm.

Cloning, Sequencing and Structural Analysis of Aptamer Sequences

The ssDNA pool of the third round of selection was cloned using a TOPO TA Kit for Sequencing (Invitrogen). The PCR products were inserted into pCRTM4-TOPO vectors and transformed into competent E. coli TOP10 cells. The positive colonies were randomly picked after overnight incubation at 37° C. on LB plates containing 50 μg/mL of kanamycin. Plasmid DNA from each colony was purified and sequenced (The Applied Genomics Centre, University of Alberta). A total of 55 colonies were picked for sequencing and 53 colonies with correct 80-base insert sequence were obtained. The secondary structure of each sequence was predicted using UNAFold (IDT), at room temperature (25° C.) and with 100 mM NaCl and 5 mM $MgCl_2$. The most probable structure of each sequence was chosen on the basis of the lowest free energy of formation (ΔG; kcal/mol).

Measurements of Binding Affinity and Dissociation by Magnetic Bead-Based Fluorescence Assay Equilibrium dissociation constants ($K_d$) were determined using a magnetic bead-based fluorescence binding assay. A ssDNA pool with FAM labeling was heated at 95° C. for 10 min and chilled on ice for another 10 min. Various concentrations of the ssDNA pool (0-75 nM) was incubated with target protein-coated magnetic beads ($10^7$ beads) at 37° C. for 30 min. To cross-link, 1% of formaldehyde was added into the mixture and incubated at room temperature for 15 min. The unbound DNA was removed by washing the beads 3 times with wash buffer. The bound DNA was released by heating at 95° C. for 10 min and was collected to quantitatively measure fluorescence using a Beckman microplate reader (Ex/Em=485 nm/515 nm). The $K_d$ value was calculated by using a one-site binding model and the equation $Y=B_{max} \times X/(K_d+X)$, where Y is the fluorescence intensity at each concentration of ssDNA, X is the concentration of FAM-labeled ssDNA, and $B_{max}$ is the fluorescence intensity at saturation.

The dissociation of protein-aptamer complexes was investigated by determining the ratio of bound aptamers before dilution and the remaining bound aptamers after dilution as a function of time. The FAM-labeled aptamer (250 nM) was denatured with heat and incubated with target protein-conjugated magnetic beads (108 beads) at 37° C. for 30 min. After removed from unbound aptamers, the complexes on magnetic beads were diluted 100× with different buffer and maintained at different temperature over a period of 120 min. At various time points the dissociated aptamers were removed from the protein-aptamer complexes on the magnetic beads by using a magnet. The bound aptamers were released by heating and the amount was measured by a microplate reader (Ex/Em=485 nm/515 nm) at each time point. The ratio of remaining bound aptamers on target protein was plotted as a function of time.

Cell Cultures

Three cell lines, SK-BR3, MCF-7 and MDA-MB-435 wt, were kindly provided by Dr. Afsaneh Lavasanifar (Faculty of Pharmacy and Pharmaceutical Sciences, University of Alberta). SK-BR-3 cells were maintained in McCoy's 5A medium supplemented with 10% (v/v) fetal bovine serum, 100 U/mL penicillin and streptomycin at 95% humidity and 5% CO2. MCF-7 and MDA-MB-435 wt cells were maintained in RPMI-1640 medium supplemented with 10% (v/v) fetal bovine serum, 100 U/mL penicillin and streptomycin at 95% humidity and 5% CO2

Fluorescence Imaging for HER2 Expressed Live Cells

Fluorescence imaging of live cells was performed on an Olympus IX-81 microscope base combined with a Yokagawa CSU X 1 spinning disk confocal scan-head and Hamamatsu EMCCD cameras with a 40×/1.3 objective. A 491 nm diode-pumped laser was used as the excitation source for carboxyfluorescein fluorescent dye (FAM) labeling and a 561 nm diode-pumped laser was used for phycoerythrin fluorescent protein (PE) labeling. SK-BR-3, MCF-7 and MDA-MB-435 wt cells were seeded and cultured in 35-mm glass bottom culture dish overnight. Prior to incubation with aptamer or antibody, cells were washed 3 times with 1 mL PBS buffer. FAM-labeled HER2 aptamer (H12, 50 nM) and PE-labeled anti-human ErbB2/HER2 monoclonal antibody (1/50 dilution) were mixed into 200 μL PBS containing 5 mM $MgCl_2$ and 10% FBS and added into cells for co-incubation at 37° C. for 30 min. The cells were washed with PBS buffer (with 0.1% BSA) for 3 times before imaging. FAM-labeled unselected DNA library were also co-incubated with PE-labeled antibodies as negative control.

Results

Aptamer Selection Based on Formaldehyde Cross-Linking

The schematic of the SELEX process based on formaldehyde cross-linking was shown in FIG. 1. Similar to the traditional SELEX process, a random-sequence DNA library (2 nmol, ~$10^{15}$ sequences) was first incubated with the target protein which was coated on magnetic beads, allowing for the formation of non-covalent protein-DNA complexes (FIG. 1A step 1). Formaldehyde was then added to generate cross-links between specific protein-DNA complexes (FIG. 1A step 2). We first examine the selectivity of the formation of formaldehyde cross-links by using PDGF-BB protein and its aptamer 20t as a model. After incubation and formaldehyde cross-linking, the complexes of PDGF-BB and aptamer 20t were separated from free aptamer in native polyacrylamide gel. The complexes bands were observed only between PDGF-BB protein and aptamer 20t (FIG. 1B). Furthermore, the intensity of bands was increased along with the increasing of concentration of PDGF-BB protein. On the contrary, there were no complexes formed between aptamer 20t and HSA protein, even at extremely high concentrations of HSA, with or without formaldehyde cross-linking. This result proved that formaldehyde specifically cross-linked only pre-formed complexes of protein and aptamer with concentration dependent.

The formation of cross-links by formaldehyde turns dynamic, non-covalent interactions between protein and DNA into stable, covalent bonds. Stringent washing conditions can then be applied to eliminate the non-specific absorption of DNA on the solid matrix without interrupting the specific DNA binding (FIG. 1A step 3). This will accelerate the process of SELEX. In this work, 6 M of urea buffer was used as stringent wash buffer. Without cross-linking, the complexes of PDGF-BB and aptamer 20t were dissociated by using urea buffer as stringent washing, which may also cause denaturation of the protein (FIG. 10). In contrast to mild washing conditions, only about 10% of bound DNA without cross-linking remained after washing by urea buffer. On the contrary, the cross-linked complexes were protected from the dissociation under stringent washing conditions. After formaldehyde cross-linking, there was no significant different between the amounts of bound DNA under mild or stringent wash conditions (FIG. 10). When PDGF-BB protein was incubated with unselected ssDNA library, the binding percentage was not increased after formaldehyde cross-linking—only less than 2%. Also, the random ssDNA library, dominated by non-binding sequences, was not artificially bound to PDGF-BB protein after cross-linking, which is another evidence for the selectivity of formaldehyde cross-linking. Therefore, stringent washing conditions (ie. urea buffer) combined with formaldehyde cross-linking can effectively eliminate the non-specific binding from 2% to less than 1%. The unbound DNA can then be removed more efficiently by preserving the complexes with formaldehyde cross-linking and stringent washing conditions. As comparison, mild conditions (HEPES binding buffer) were chosen in the traditional SELEX to remove the unbound DNA without breaking the interaction of protein-DNA complexes.

Figure 1B:
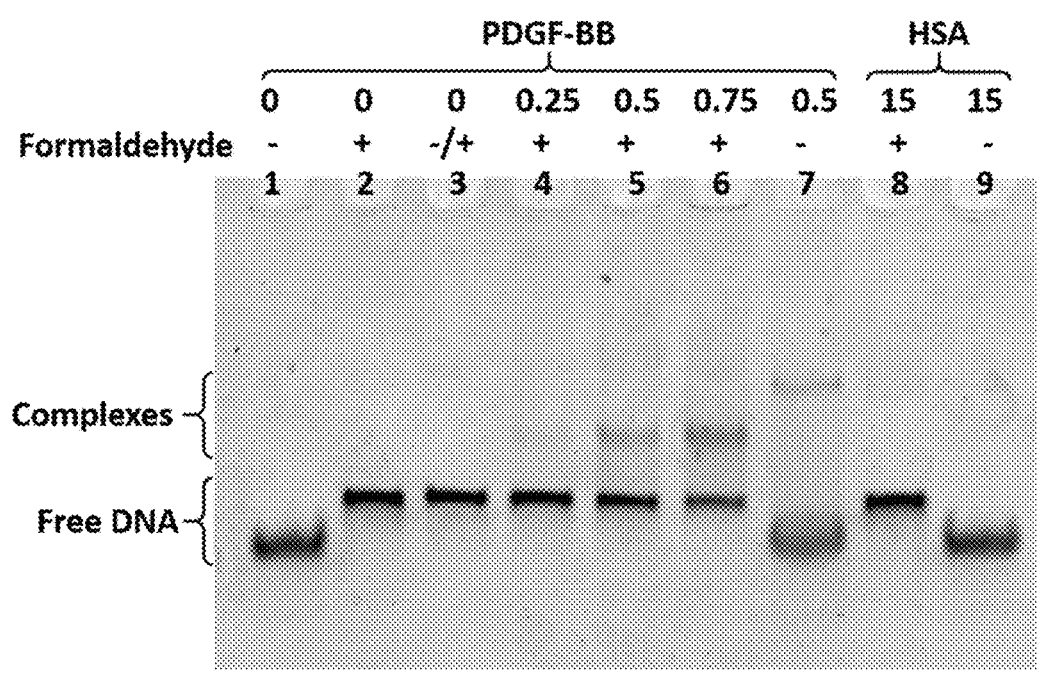
FIG. 1B Selectivity of formaldehyde cross-linking. Aptamer 20t only formed the cross-linked complexes by formaldehyde with its target PDGF-BB protein, not with non-binding protein HSA. Lane 1: 20t aptamer (2 μM); lane 2: 20t with $CH_2O$ (1%); lane 3: 20t with $CH_2O$ and quencher glycine (125 nM); lane 4: 20t and PDGF-BB (0.25 μM) with $CH_2O$; lane 5: 20t and PDGF-BB (0.5 μM) with $CH_2O$; lane 6: 20t and PDGF-BB (0.75 μM) with $CH_2O$; lane 7: 20t and PDGF-BB (0.5 μM) without $CH_2O$; lane 8: 20t and HSA (15 μM) with $CH_2O$; lane 9: 20t and HSA (15 μM) without $CH_2O$.
Figure 1C:
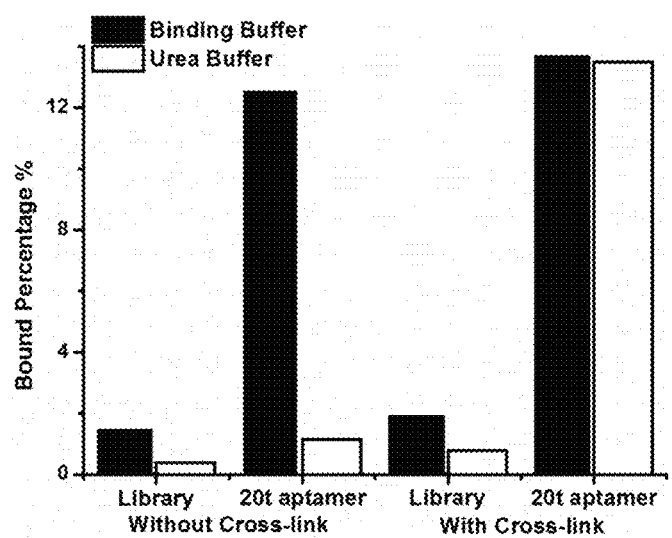
FIG. 1C Washing conditions combined with formaldehyde cross-linking. With or without formaldehyde cross-linking, the bound percentage of initial library or aptamer 20t on PDGF-BB coated magnetic beads were determined after washing with different buffers: binding buffer or urea buffer.
Figure 1D:
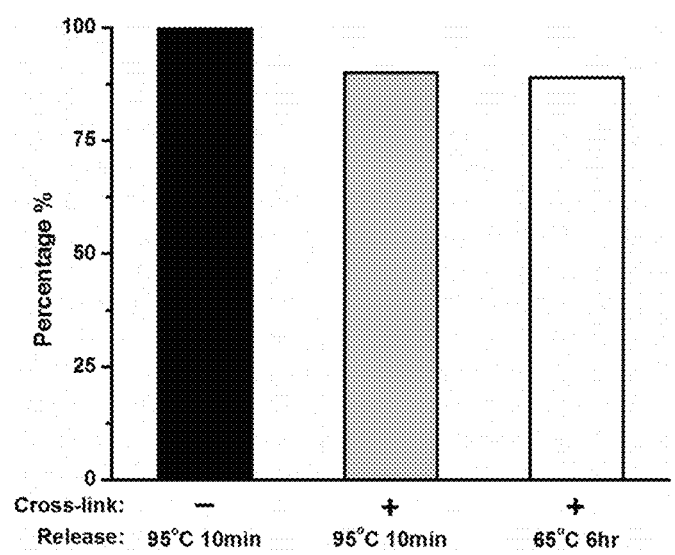
FIG. 1D Reversibility of formaldehyde cross-linking. The bound ssDNA from complexes with or without formaldehyde cross-linking were releasing by heating.

After the removal of unbound DNA, the bound DNA was released by heating at 95° C. for 10 min (FIG. 1A step 4). Formaldehyde cross-linking is fully reversible at high temperatures (>60° C.) in aqueous solutions (36). Similar to the release of apatmer from complexes without cross-linking, most of the bound aptamer after cross-linking (~90%) was released by heating at 95° C. for only 10 min or at 65° C. for 6 hours (FIG. 1D). These results demonstrated that ssDNA can be released from complexes by heating which reverses the cross-linking and breaks the protein-aptamer complexes. Furthermore, the released DNA can be amplified directly by polymerase chain reaction (PCR) without interference by formaldehyde. Finally, the ssDNA pool was generated from the double-stranded PCR product for next round of selection (FIG. 1A step 5 & 6). In all, FIG. 1A shows the small alteration of adding formaldehyde after the incubation step as in contrast to the traditional SELEX process. This means that formaldehyde cross-linking can be easy to incorporate into any type of SELEX.

Formaldehyde Cross-Linking can Accelerate the Progress of SELEX

Figure 2A:
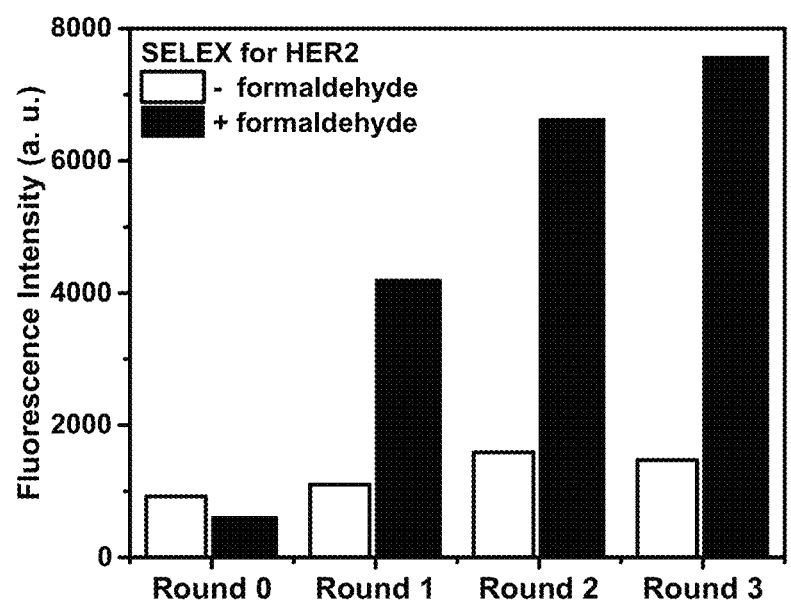
FIG. 2A is bulk dissociation constants ($K_d$) of enriched ssDNA pool against HER2 protein after each round of selection with or without formaldehyde cross-linking. HER2-coated magnetic beads ($10^7$ beads) were used in this experiment.
Figure 2B:
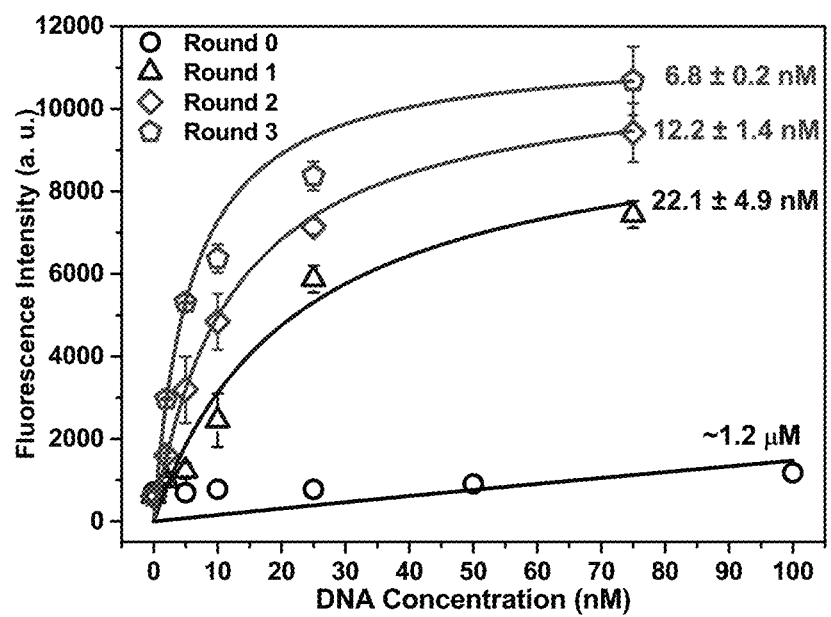
FIG. 2B is the $K_d$ measured by a magnetic bead-based fluorescence binding assay. HER2-coated magnetic beads ($10^7$ beads) were used in this experiment.

To demonstrate the proof-of-principle, human epidermal growth factor receptor 2 (HER2/ErbB2) was chosen as a model target because it is both an important biomarker and a target of therapy for breast cancer (37-39). We performed three rounds of SELEX for HER2 protein with or without formaldehyde cross-linking. Through three rounds of selection with formaldehyde cross-linking, more FAM-labeled ssDNA bound to HER2 protein progressively (FIG. 2A). The fluorescence intensity of bound ssDNA after first round is 6.8-fold higher than the initial library. However, there was not obviously increase of bound ssDNA from SELEX without formaldehyde. Then we determined the bulk $K_d$ of the enriched ssDNA pool from SELEX with formaldehyde cross-linking by a magnetic bead-based fluorescence binding assay. Initially, the ssDNA library displayed no obvious binding, with a $K_d$ of over 1 µM. After only one round of selection, the bulk binding affinity ($K_d$) reached 22.1 ±4.9 nM, which was 54-fold lower than that of initial ssDNA library. Finally, the binding affinity of DNA pool to HER2 was determined to be 6.8±0.2 nM after three rounds of selection (FIG. 2B). The enrichment of the high affinity binding sequence was observed during three rounds of SELEX with formaldehyde cross-linking. The acceptable DNA pool with binding affinity at nM range can obtain using only single round of SELEX. These results demonstrated that the high-affinity binding sequence could be efficiently enriched from the initial random sequence library after only three rounds by using SELEX with formaldehyde cross-linking.

SELEX with formaldehyde cross-linking has been proven to be a universal method for different target proteins. The five more protein targets, human platelet-derived growth factor-BB (PDGF-BB) (FIG. 2C), human immunoglobulin E (IgE) (FIG. 2D), ubiquitin (FIG. 2E), cytotoxic T-lymphocyte-associated protein 4 (CTLA-4) (FIG. 2F) and programmed death-ligand 1 (PD-L1) (FIG. 2G), are different in molecular weight and isoelectric point (pI) (Table 3).

TABLE 3

Molecular weight and isoelectric point (pI) of target proteins.

| | Molecular weight | Isoelectric point (pI) |
|---|---|---|
| Epidermal growth factor receptor 2 (ErbB2/HER2) | 137.9 kDa | 5.58 |
| Platelet-derived growth factor-BB (PDGF-BB) | 27.3 kDa | 9.39 |
| Immunoglobulin E (IgE) | 190 kDa | 9.0 |
| Ubiquitin | 8.6 kDa | 6.56 |
| Cytotoxic T-lymphocyte-associated protein 4 (CTLA-4) | 24.6 kDa | 6.7 |
| Programmed death-ligand 1 (PD-L1) | 33.3 kDa | 6.76 |

Figure 2C:
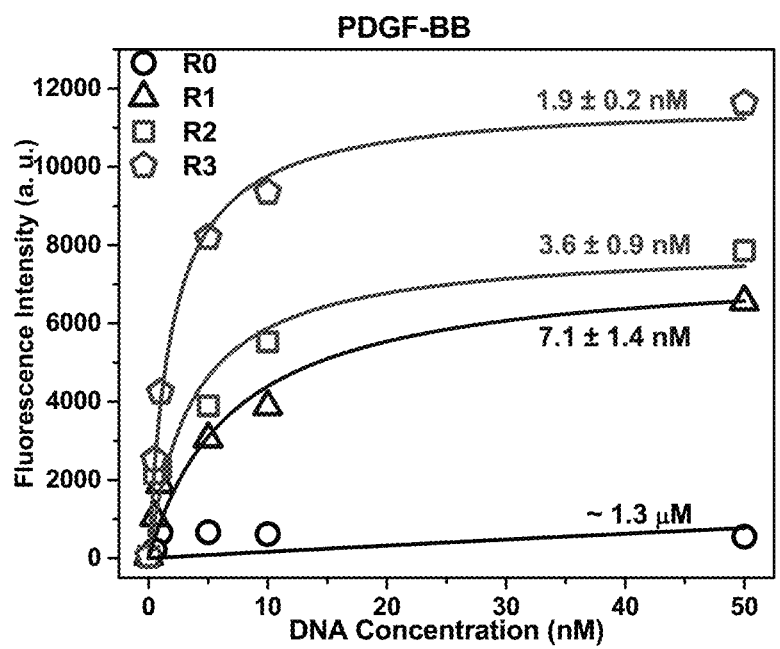
FIG. 2C Dissociation constants ($K_d$) of enriched ssDNA pool after each round of selection—PDGF-BB.
Figure 2D:
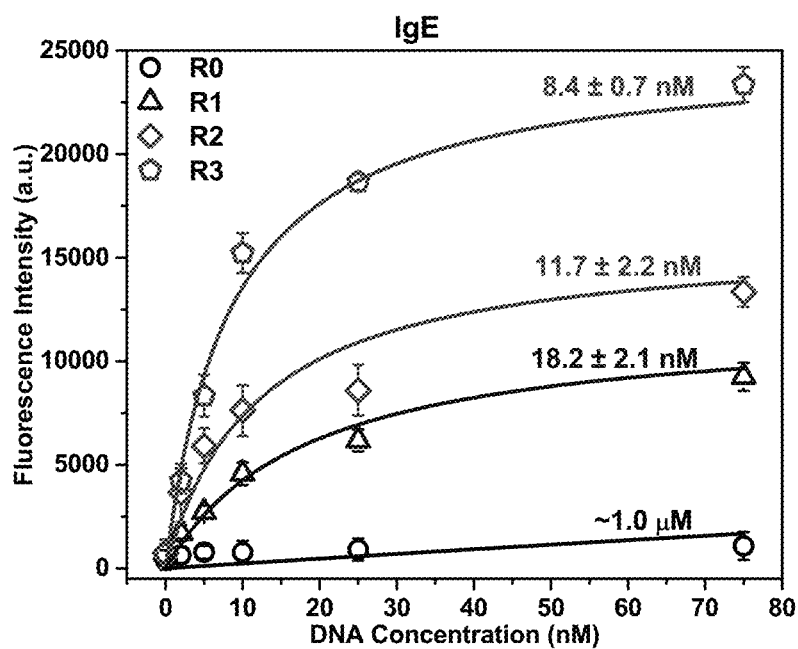
FIG. 2D Dissociation constants ($K_d$) of enriched ssDNA pool after each round of selection—IgE.
Figure 2E:
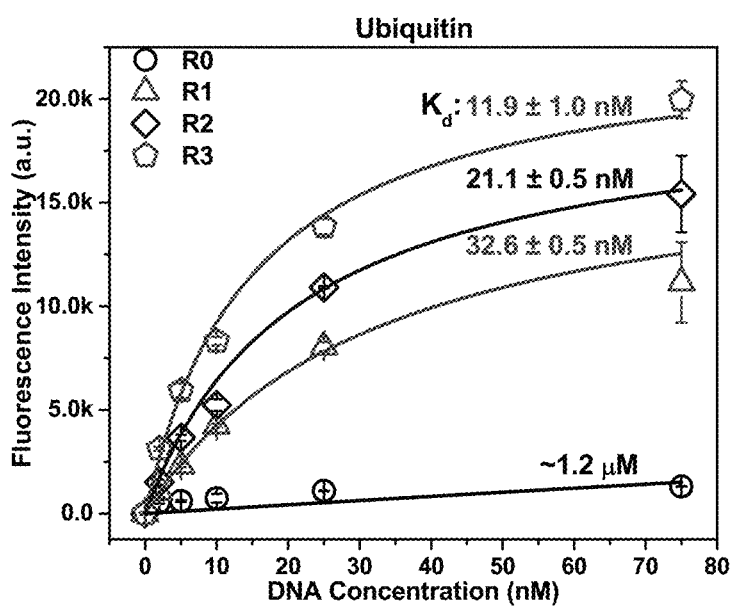
FIG. 2E Dissociation constants ($K_d$) of enriched ssDNA pool after each round of selection—ubiquitin.
Figure 2F:
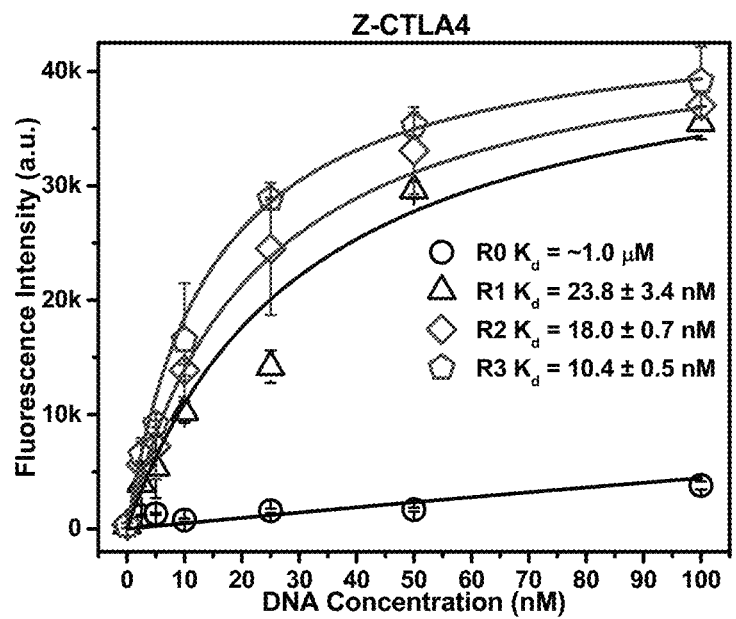
FIG. 2F Dissociation constants ($K_d$) of enriched ssDNA pool after each round of selection—CTLA4.
Figure 2G:
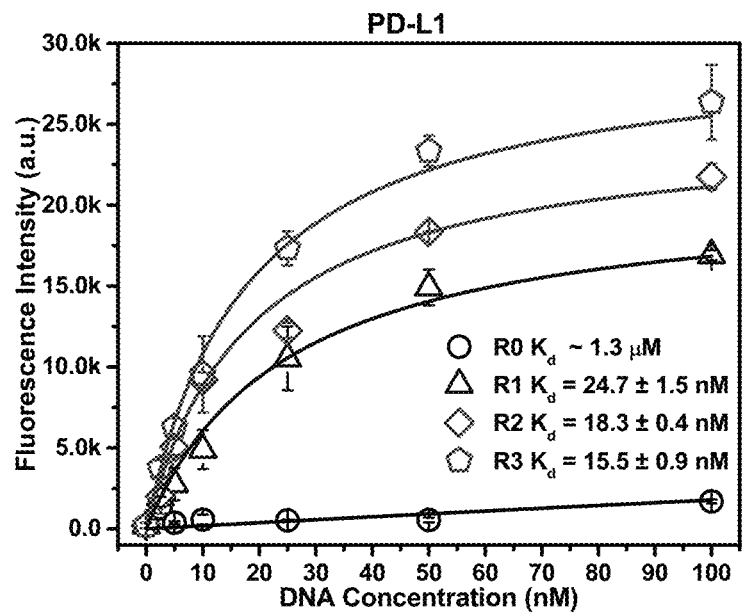
FIG. 2G Dissociation constants ($K_d$) of enriched ssDNA pool after each round of selection—PD-L1.

Despite these differences, high-affinity aptamers were obtained for all of five target proteins through only three rounds of SELEX based on formaldehyde cross-linking. The bulk $K_d$ value of round 3 pools against PDGF-BB, IgE, ubiquitin, CTLA4 and PD-L1 protein was 1.9±0.2 nM, 8.4±0.7 nM, 11.9±1.0 nM, 10.4±0.5 nM, and 15.5±0.9 nM, respectively (FIG. 2C). Even after single round of SELEX, the bulk Kds reached to nM range, which were 32 to 170-fold lower than that of the initial ssDNA library. For PDGF-BB and IgE protein, the binding affinity of ssDNA pool from the third round was comparable to previously reported aptamers that were obtained after 10-15 rounds of selection using the original SELEX method (42, 43). These results reveal that the discovery of high affinity aptamers can be greatly accelerated by using the improved SELEX with formaldehyde cross-linking.

Figure 2H:
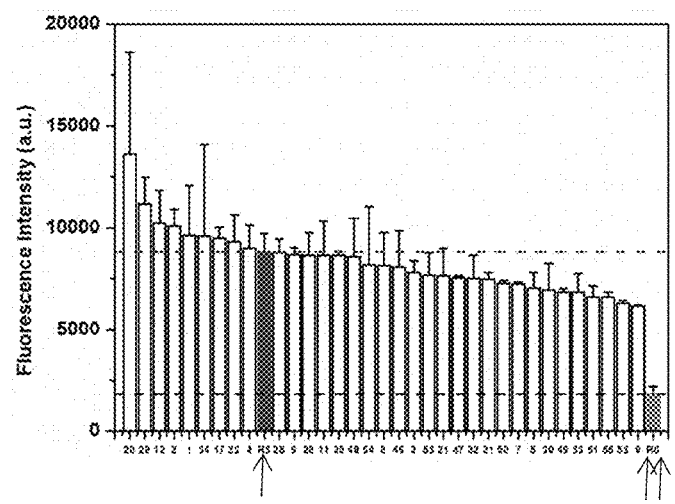
FIG. 2H Screening the binding intensity of each sequence. Single arrow denotes round 3 pool, and double arrow denotes grey bar is unselected library. FAM-labeled aptamers (10 nM) and HER2-coated magnetic beads ($10^7$ beads) were used in this experiment.
Figure 2I:
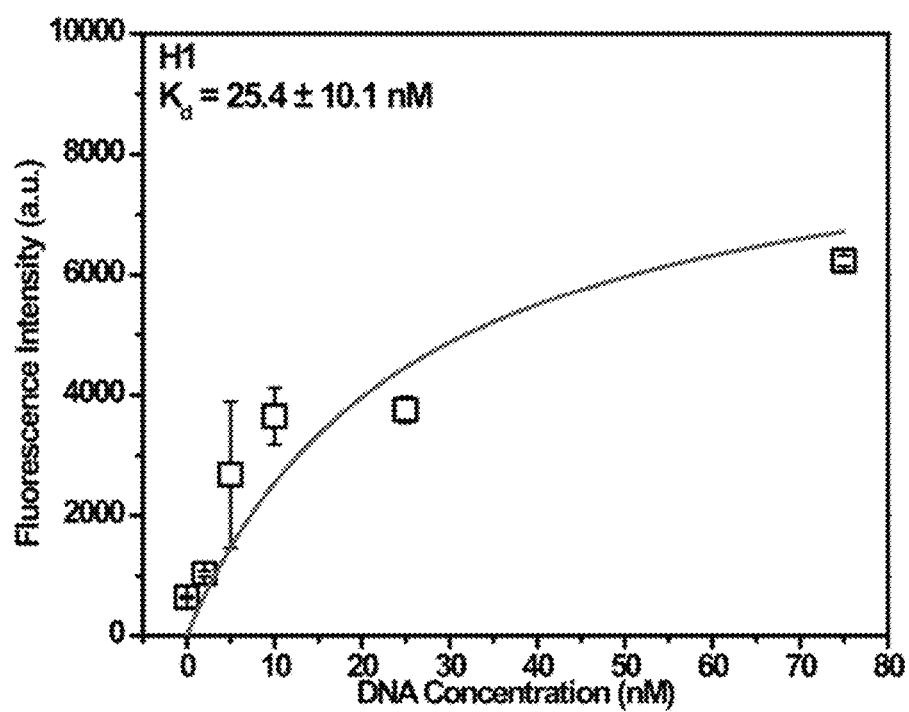
FIG. 2I Dissociation constants and secondary structures of H1 (SEQ ID NO: 1). In this experiment, $10^7$ of HER2-coated magnetic beads were used. The secondary structure of each sequence was analyzed using UNAFold (IDT), with input conditions of room temperature (25° C.), 100 mM NaCl and 5 mM $MgCl_2$. The most likely structure of each sequence was chosen on the basis of the lowest predicted free energy of formation ($\Delta G$; kcal/mol).
Figure 2I:
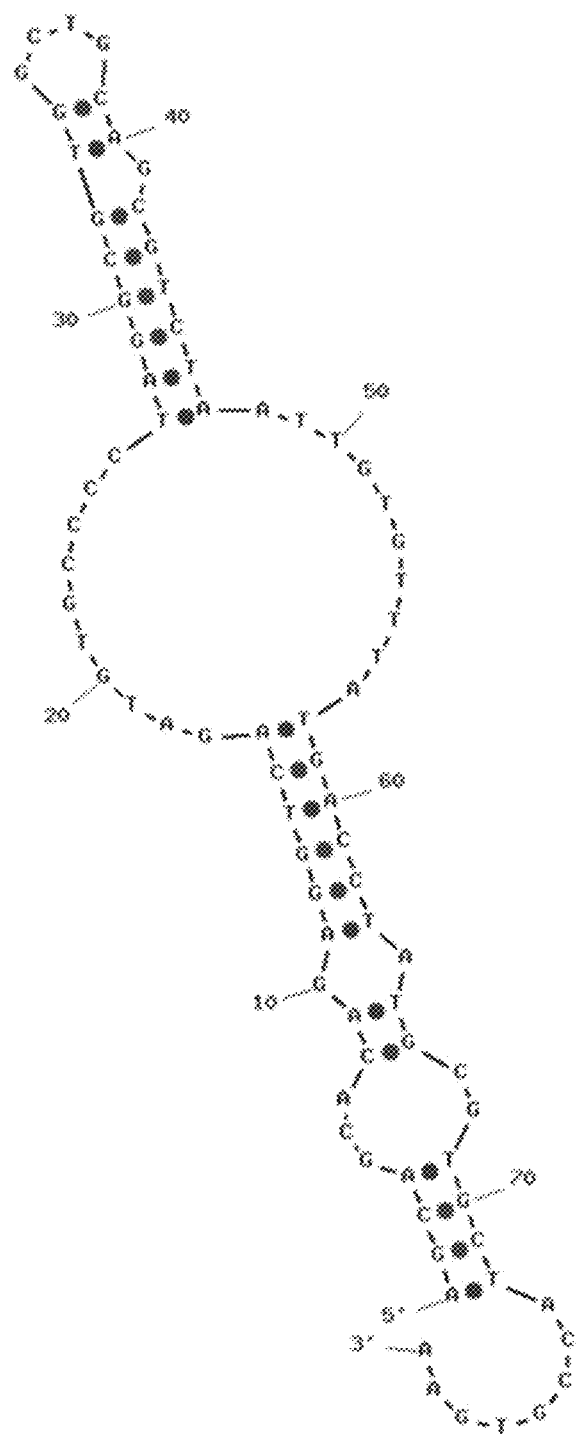
Figure 2J:
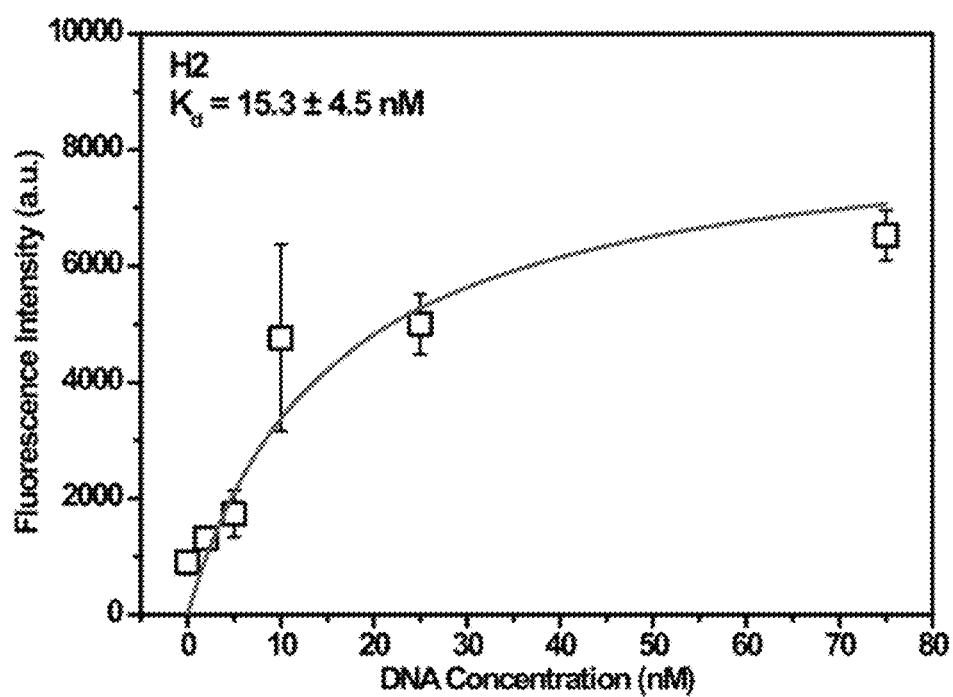
FIG. 2J Dissociation constants and secondary structures of H2 (SEQ ID NO: 2). In this experiment, $10^7$ of HER2-coated magnetic beads were used. The secondary structure of each sequence was analyzed using UNAFold (IDT), with input conditions of room temperature (25° C.), 100 mM NaCl and 5 mM $MgCl_2$. The most likely structure of each sequence was chosen on the basis of the lowest predicted free energy of formation ($\Delta G$; kcal/mol).
Figure 2J:
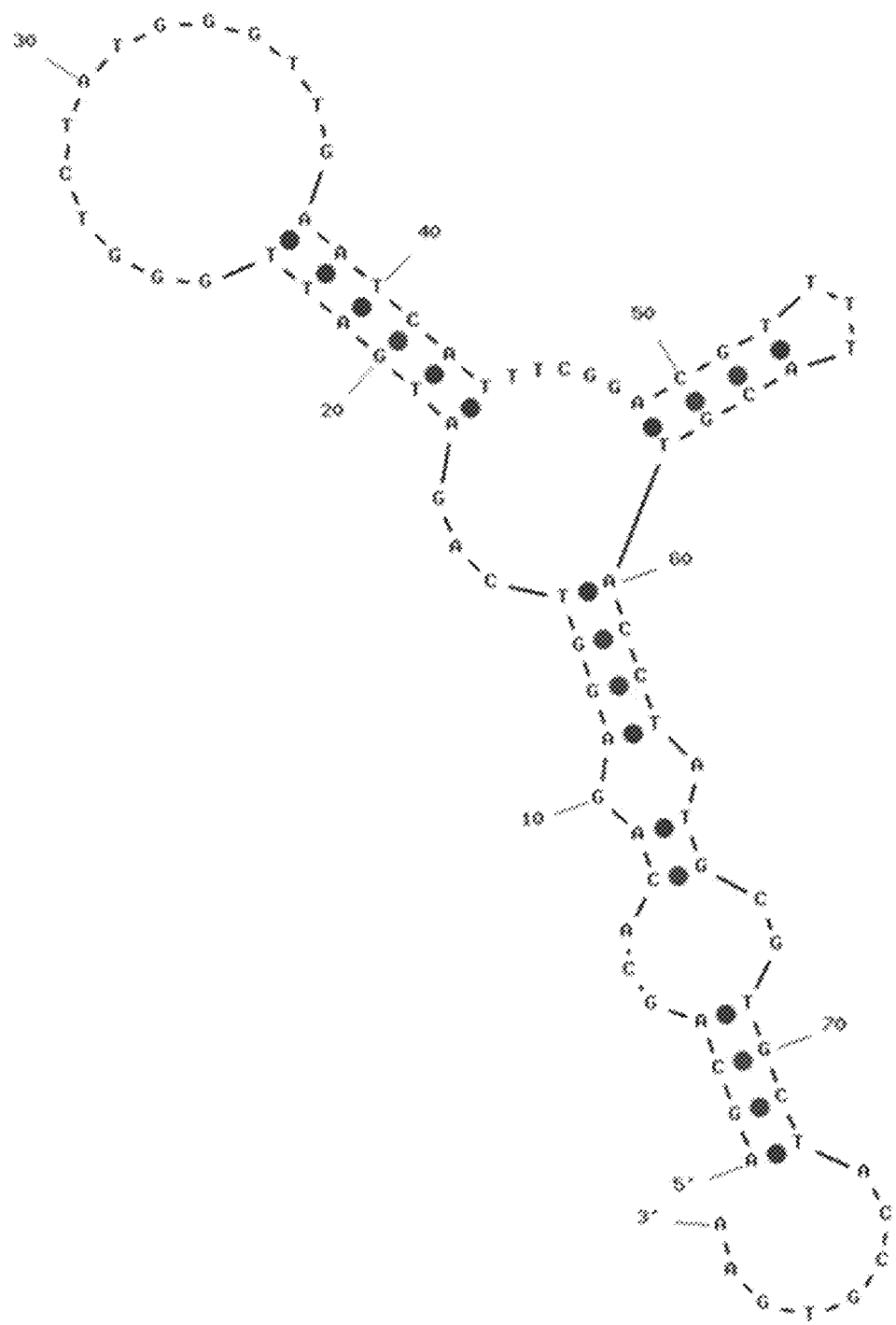
Figure 2K:
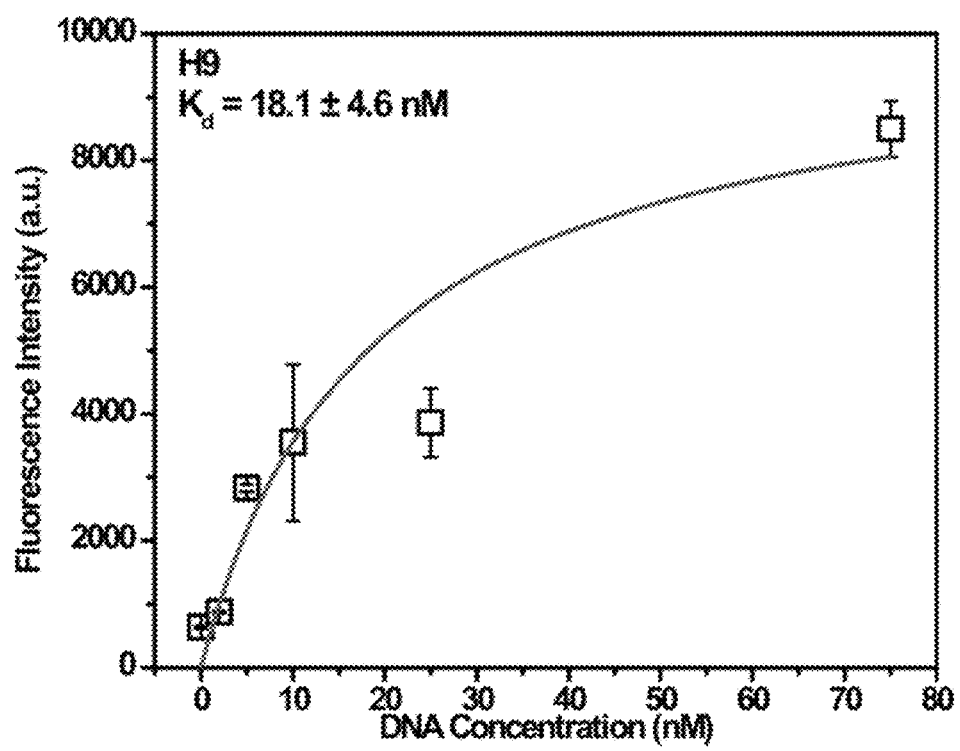
FIG. 2K Dissociation constants and secondary structures of H9 (SEQ ID NO: 9). In this experiment, $10^7$ of HER2-coated magnetic beads were used. The secondary structure of each sequence was analyzed using UNAFold (IDT), with input conditions of room temperature (25° C.), 100 mM NaCl and 5 mM $MgCl_2$. The most likely structure of each sequence was chosen on the basis of the lowest predicted free energy of formation ($\Delta G$; kcal/mol).
Figure 2K:
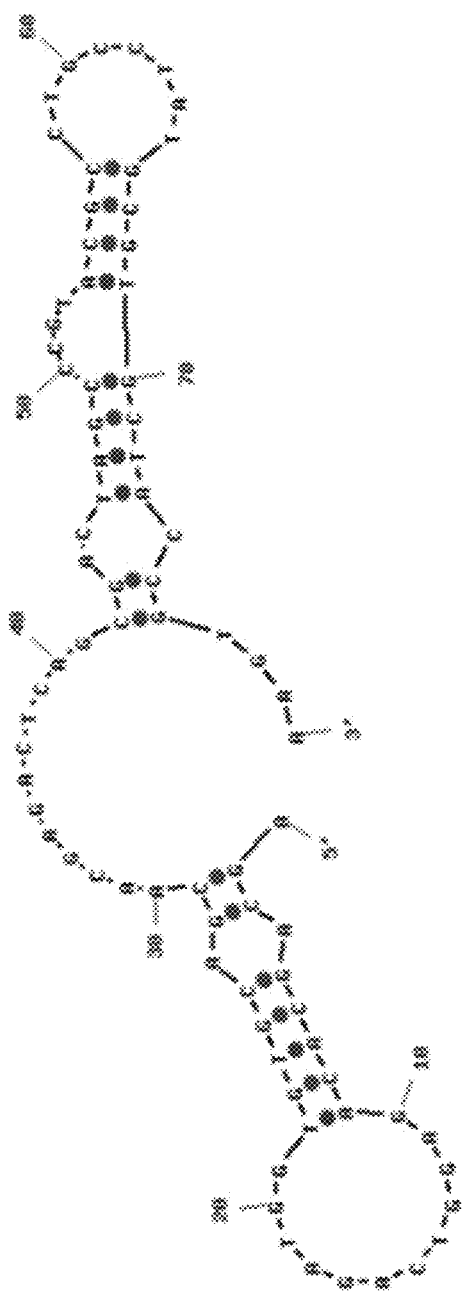
Figure 2L:
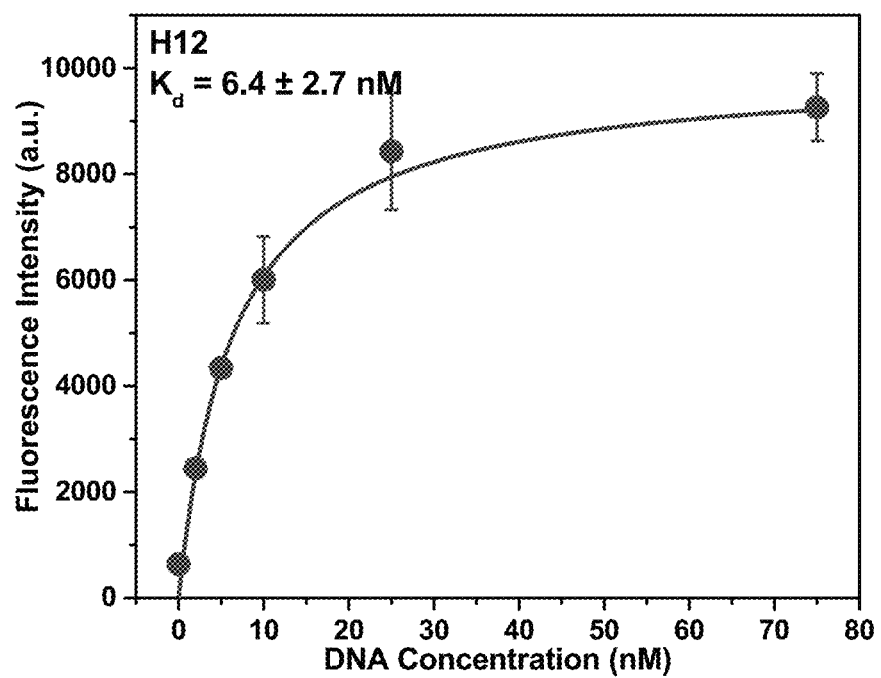
FIG. 2L Dissociation constants and secondary structures of H12 (SEQ ID NO: 13). In this experiment, $10^7$ of HER2-coated magnetic beads were used. The secondary structure of each sequence was analyzed using UNAFold (IDT), with input conditions of room temperature (25° C.), 100 mM NaCl and 5 mM $MgCl_2$. The most likely structure of each sequence was chosen on the basis of the lowest predicted free energy of formation ($\Delta G$; kcal/mol).
Figure 2L:
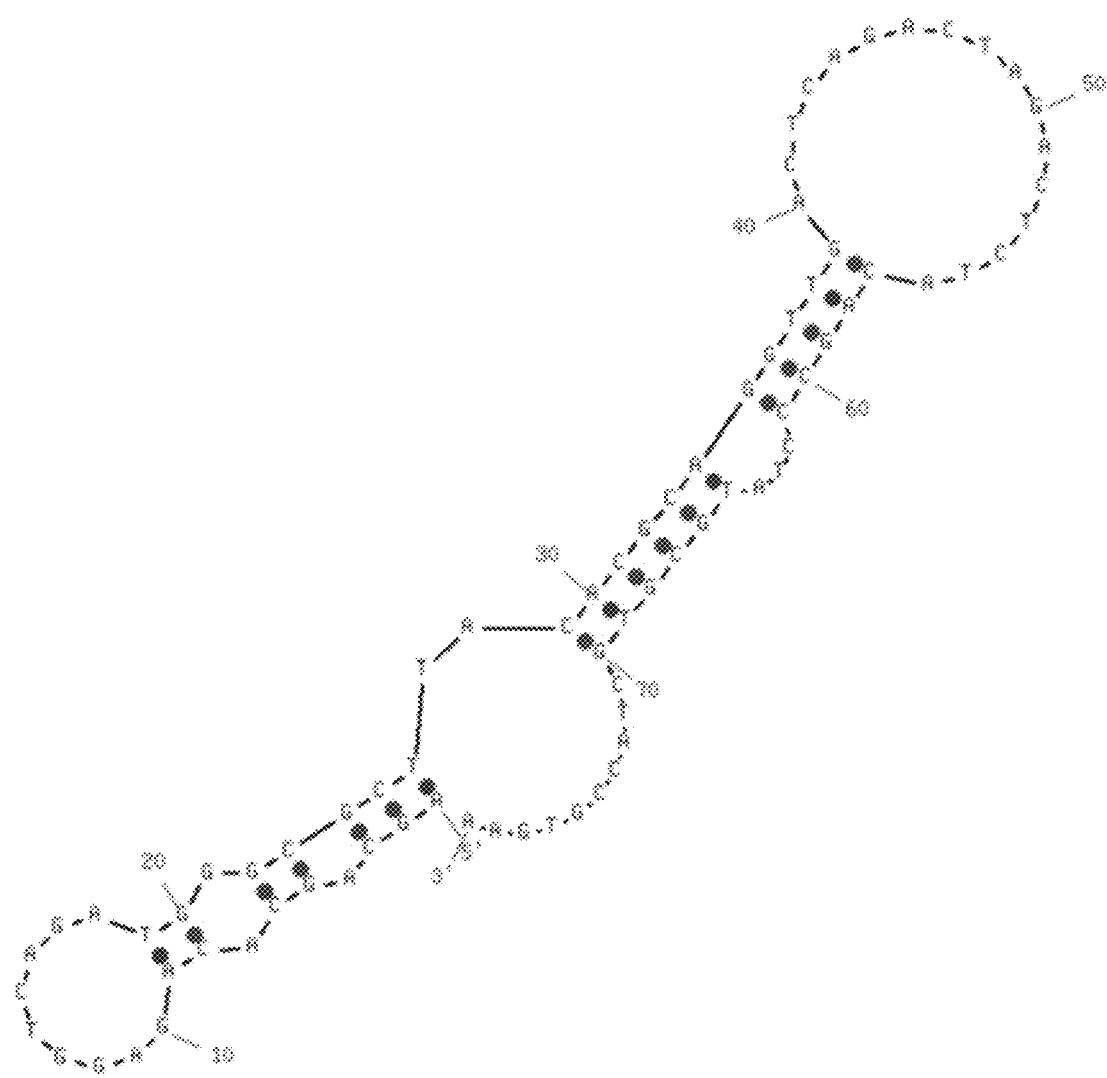
Figure 2M:
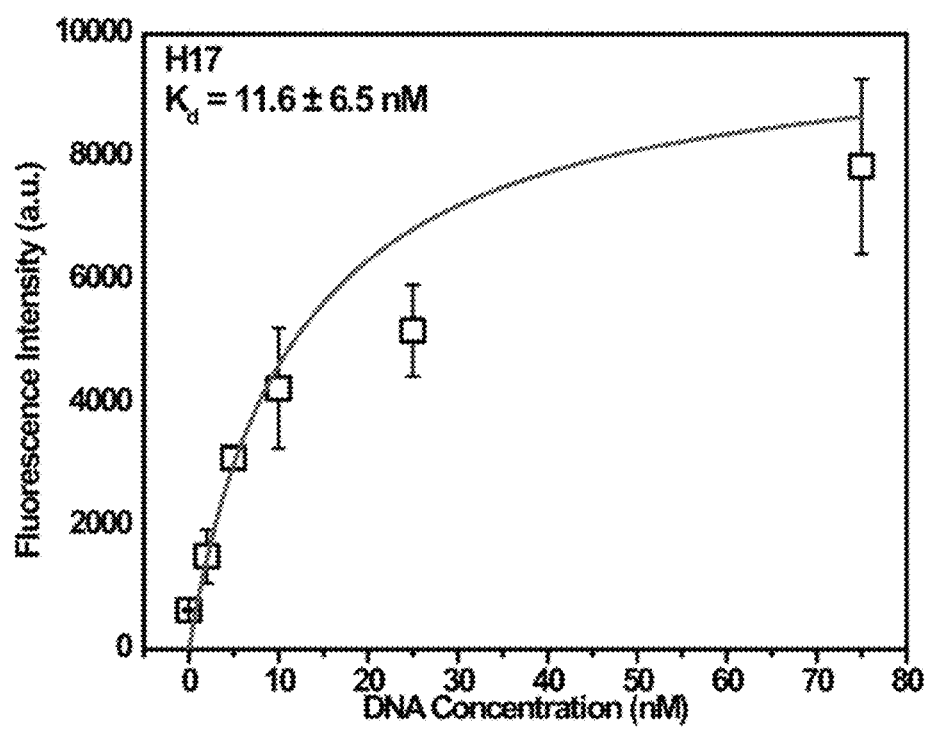
FIG. 2M Dissociation constants and secondary structures of H17 (SEQ ID NO: 24). In this experiment, $10^7$ of HER2-coated magnetic beads were used. The secondary structure of each sequence was analyzed using UNAFold (IDT), with input conditions of room temperature (25° C.), 100 mM NaCl and 5 mM $MgCl_2$. The most likely structure of each sequence was chosen on the basis of the lowest predicted free energy of formation ($\Delta G$; kcal/mol).
Figure 2M:
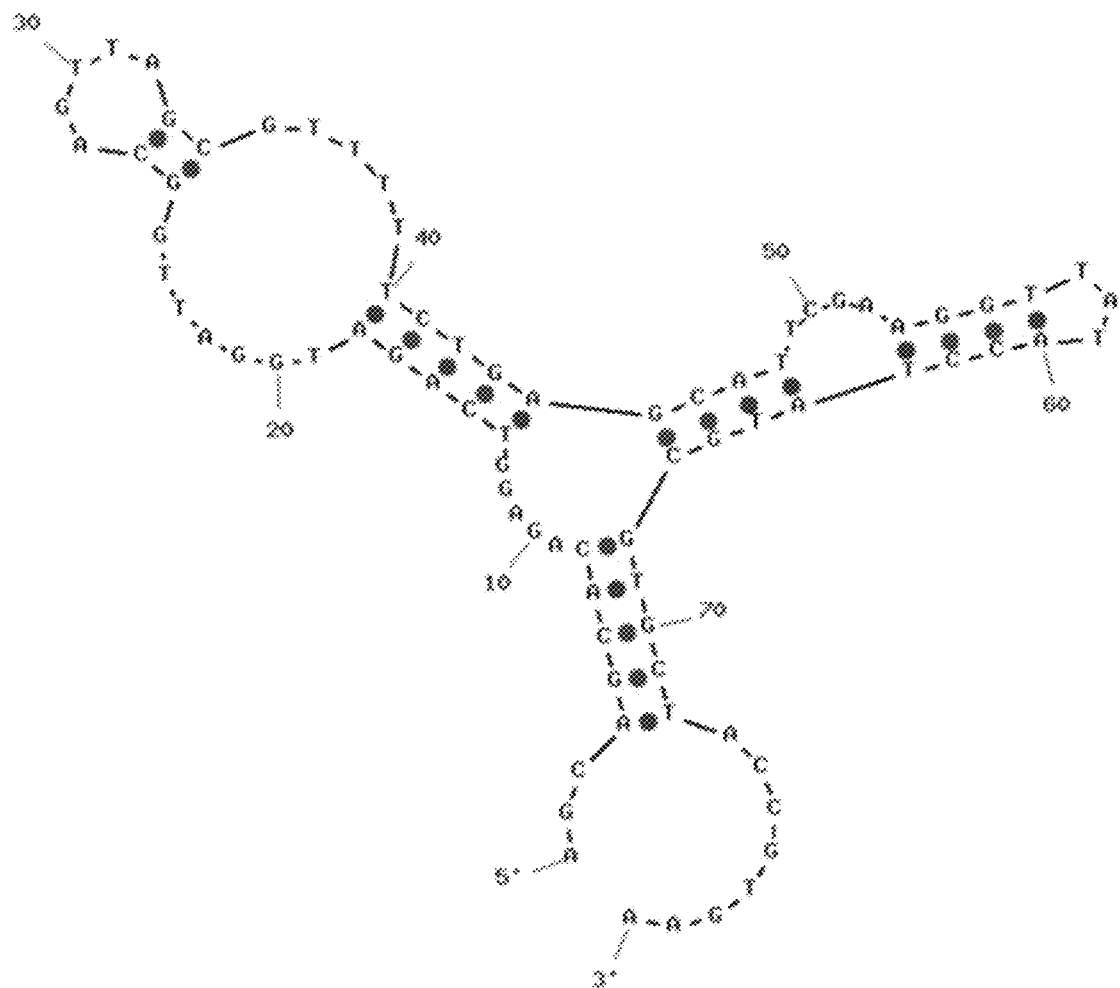
Figure 2N:
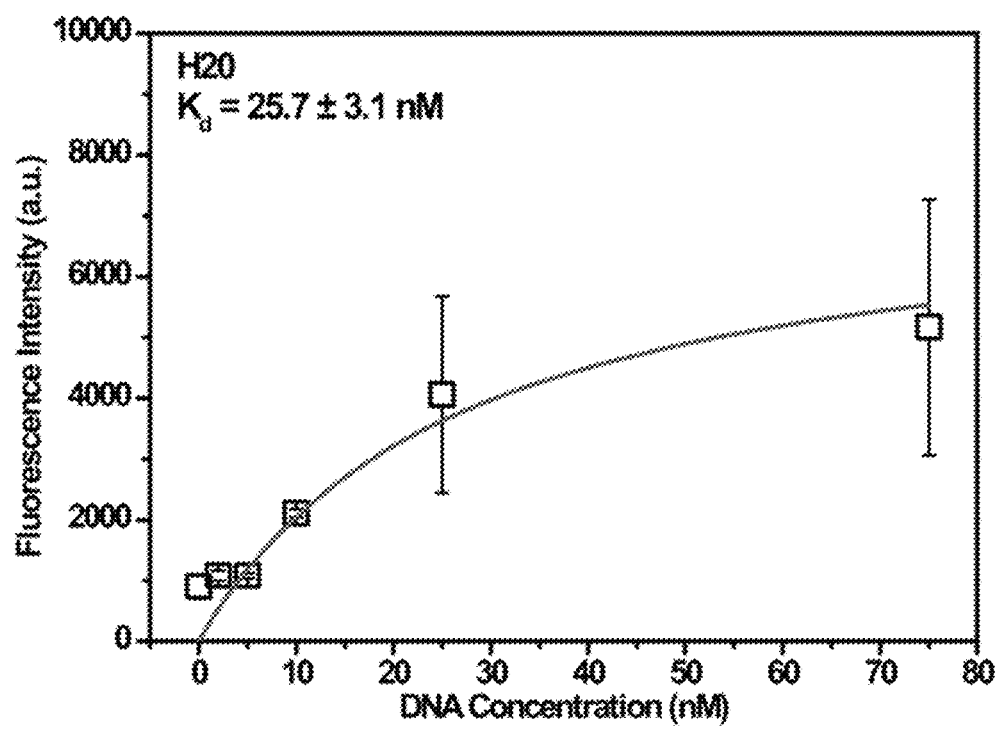
FIG. 2N Dissociation constants and secondary structures of $H_2O$ (SEQ ID NO: 26). In this experiment, $10^7$ of HER2-coated magnetic beads were used. The secondary structure of each sequence was analyzed using UNAFold (IDT), with input conditions of room temperature (25° C.), 100 mM NaCl and 5 mM $MgCl_2$. The most likely structure of each sequence was chosen on the basis of the lowest predicted free energy of formation ($\Delta G$; kcal/mol).
Figure 2N:
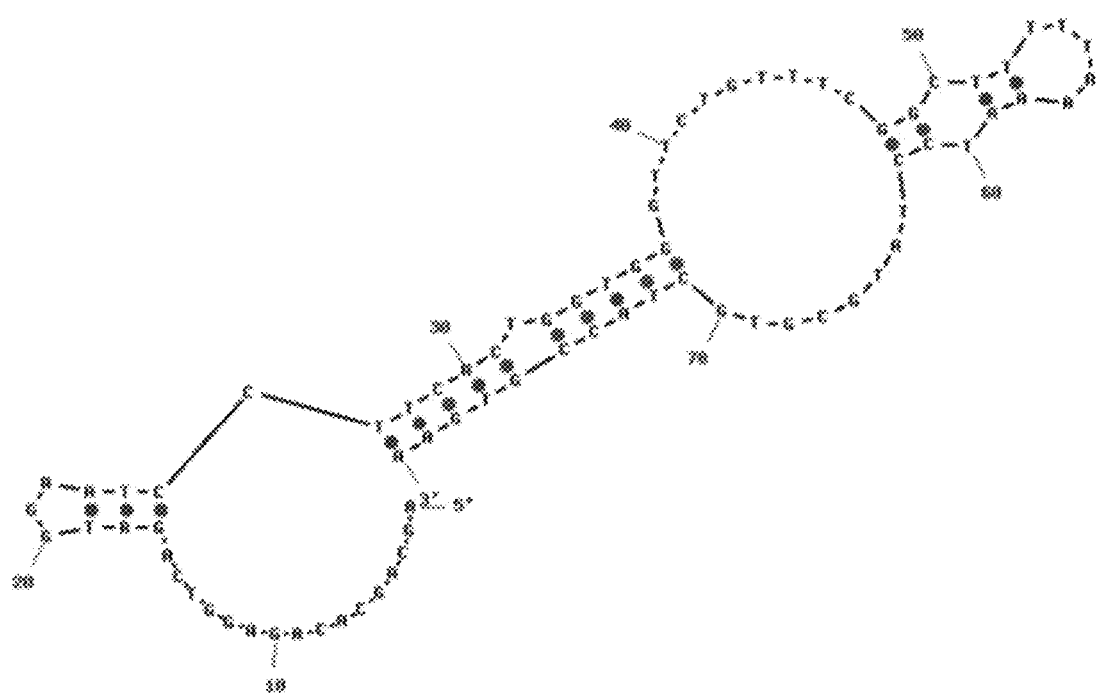
Figure 2O:
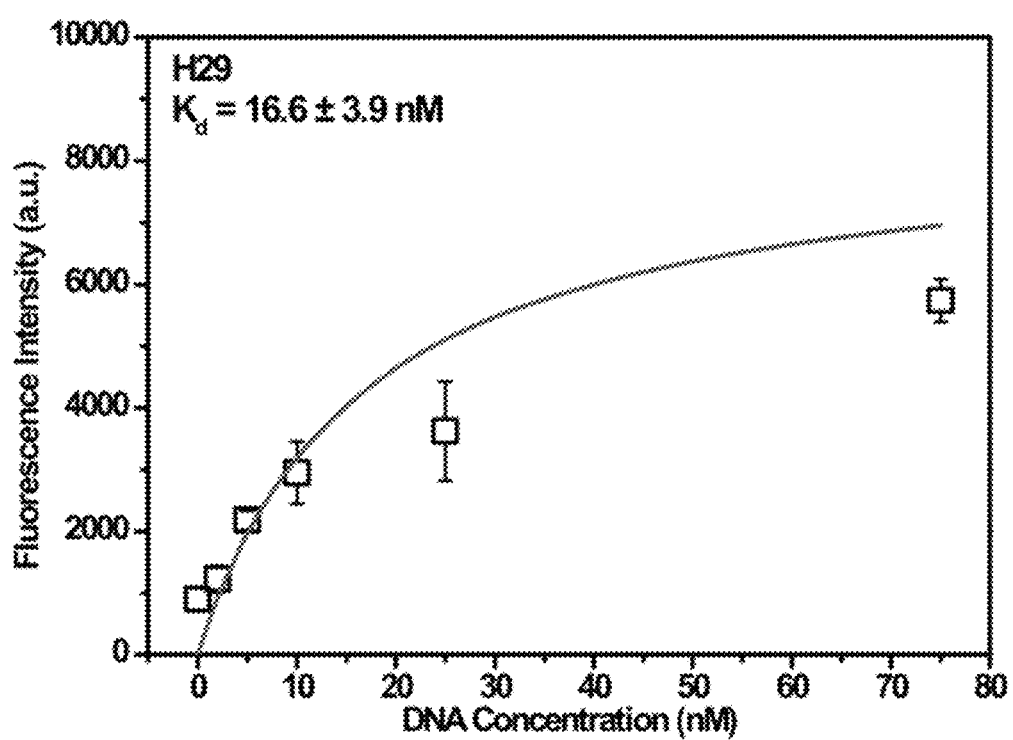
FIG. 2O Dissociation constants and secondary structures of H29 (SEQ ID NO: 37). In this experiment, $10^7$ of HER2-coated magnetic beads were used. The secondary structure of each sequence was analyzed using UNAFold (IDT), with input conditions of room temperature (25° C.), 100 mM NaCl and 5 mM $MgCl_2$. The most likely structure of each sequence was chosen on the basis of the lowest predicted free energy of formation ($\Delta G$; kcal/mol).
Figure 2O:
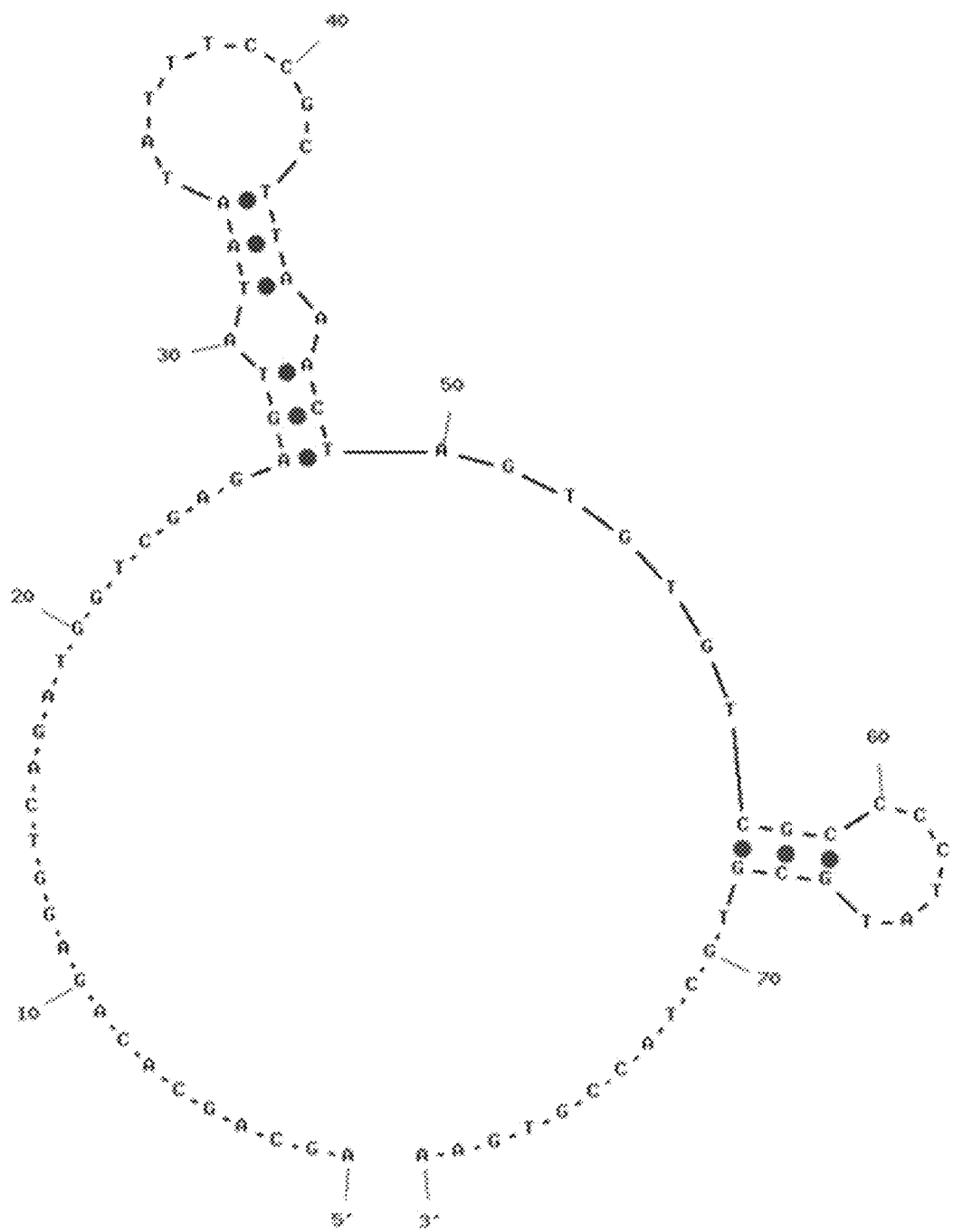
Figure 2P:
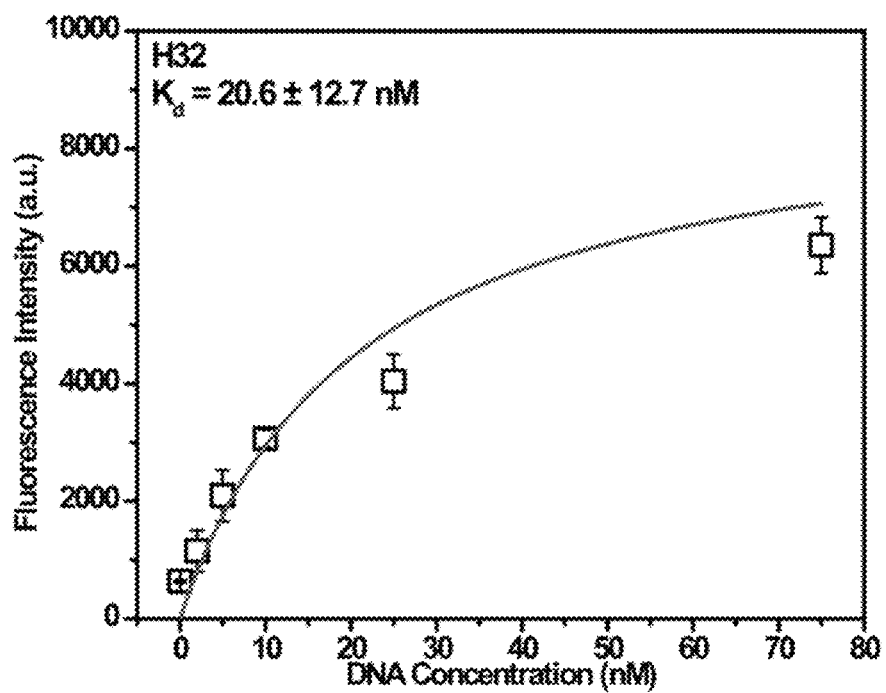
FIG. 2P Dissociation constants and secondary structures of H32 (SEQ ID NO: 40). In this experiment, $10^7$ of HER2-coated magnetic beads were used. The secondary structure of each sequence was analyzed using UNAFold (IDT), with input conditions of room temperature (25° C.), 100 mM NaCl and 5 mM $MgCl_2$. The most likely structure of each sequence was chosen on the basis of the lowest predicted free energy of formation ($\Delta G$; kcal/mol).
Figure 2P:
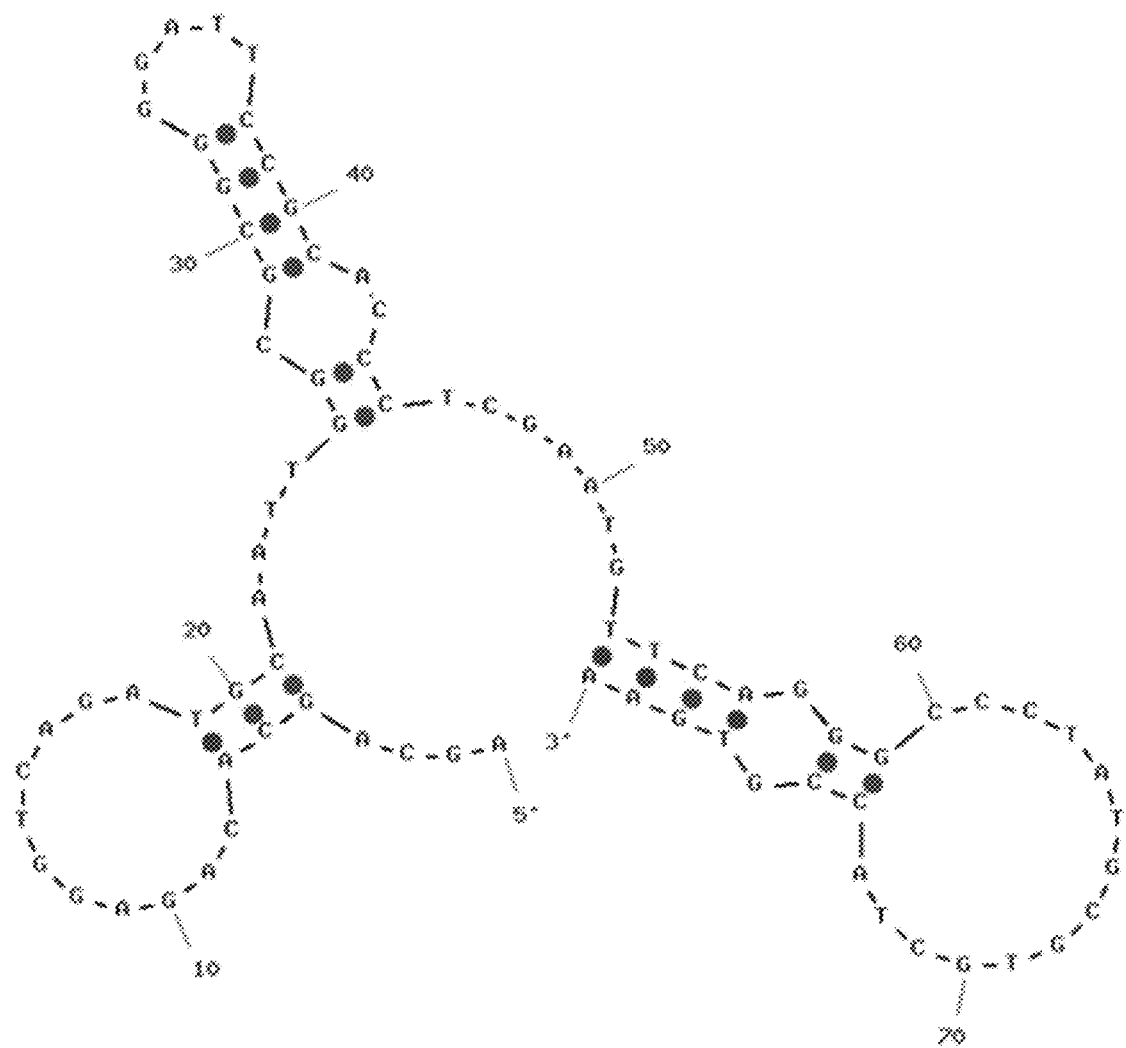

To identify the aptamer sequences against HER2 protein, the ssDNA pool after the third round of SELEX with formaldehyde cross-linking was PCR-amplified and cloned into E. coli cells for sequencing by using a TA cloning kit (Invitrogen). A total of 55 positive clones were randomly picked, and 53 sequences were obtained with the correct 80-bp insert. Among them, 28 sequences were unique and 6 sequences repeated more than once; particularly, the sequence H12 repeated 11 times. To screen the binding affinities of the different sequences, we measured the binding of each sequence with HER2 protein at a fixed concentration by using magnetic bead-based fluorescence binding assays. The different sequences were ranked on the basis of the fluorescence signal from bound DNA on HER2-coated magnetic beads (FIG. 2H). The fluorescence intensities of the different sequences showed a wide range, but all were 3.5-7.0 times higher than that of the unselected ssDNA library. The dissociation constant ($K_d$) values were further measured for eight potential sequences that showed higher relative binding than the round 3 pool (FIG. 2I, FIG. 2J, FIG. 2K, FIG. 2L, FIG. 2M, FIG. 2N, FIG. 2O, FIG. 2P). Among them, H12 (SEQ ID NO: 13) showed lowest $K_d$ values of 6.4±2.7 nM.

Figure 3A:
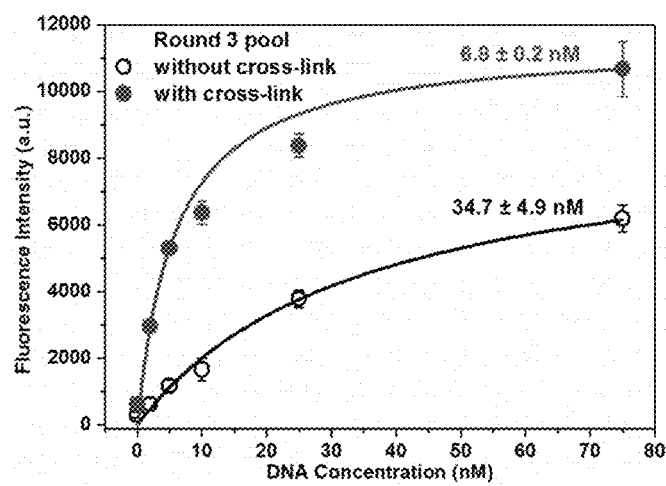
FIG. 3A is Dissociation constants ($K_d$) of third round pool with or without formaldehyde cross-linking. The $K_d$ measured by a magnetic bead-based fluorescence binding assay. HER2-coated magnetic beads ($10^7$ beads) were used in this experiment.
Figure 3B:
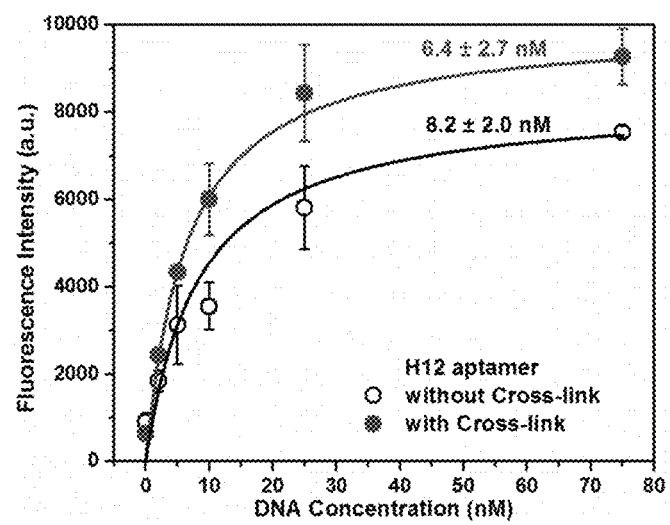
FIG. 3B is Dissociation constants ($K_d$) of sequence H12 with or without formaldehyde cross-linking. The $K_d$ measured by a magnetic bead-based fluorescence binding assay. HER2-coated magnetic beads ($10^7$ beads) were used in this experiment.

Formaldehyde Cross-Linking can Reduce the Dissociation of Protein-Aptamer Complexes The formation of cross-links by formaldehyde can turn dynamic, non-covalent interactions between target protein and aptamer into stable, covalent bonds which can significantly reduce the dissociation of complexes. We determined the binding affinity ($K_d$) of the round 3 pool and H12 to HER2 with or without formaldehyde cross-linking. With formaldehyde cross-linking, the $K_d$ of the round 3 pool was 6.8±0.2 nM, which is about 5-fold lower than the $K_d$ without cross-linking (FIG. 3A). When formaldehyde was not used, the saturated fluorescence intensity is only half of that with formaldehyde cross-linking. In contrast, the binding affinity of the H12 aptamer to the HER2 protein displayed no significant difference with or without using formaldehyde cross-linking. The $K_d$ value of H12 was 6.4±2.7 nM with formaldehyde cross-linking, whereas the $K_d$ value was 8.2±2.0 nM without formaldehyde (FIG. 3B). Although the H12 aptamer was the dominant and high-affinity sequence, there were still some weakly binding sequences in the round 3 pool. These low-affinity binding sequences may dissociate from the complexes during the experiment. The stabilization of low-affinity aptamer by formaldehyde cross-linking may contribute to the increase of $K_d$ and saturated fluorescence intensity of third round ssDNA pool.

Figure 4A:
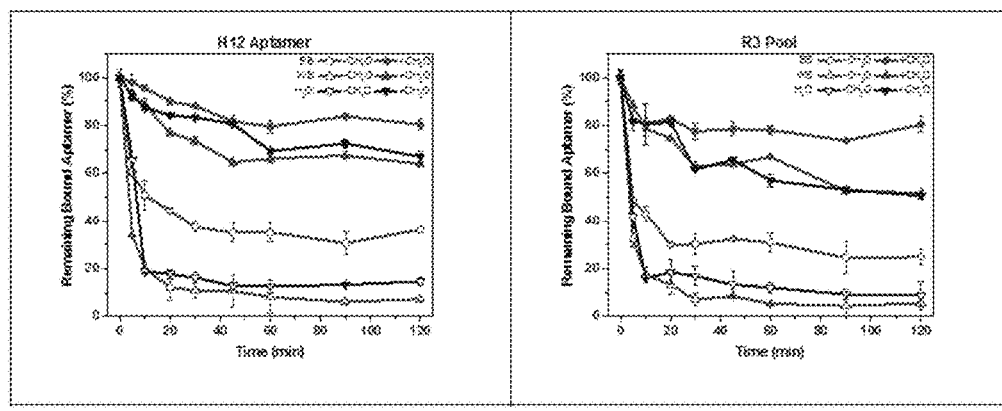
FIG. 4A Dissociation of round 3 pool against HER2.
Figure 4B:
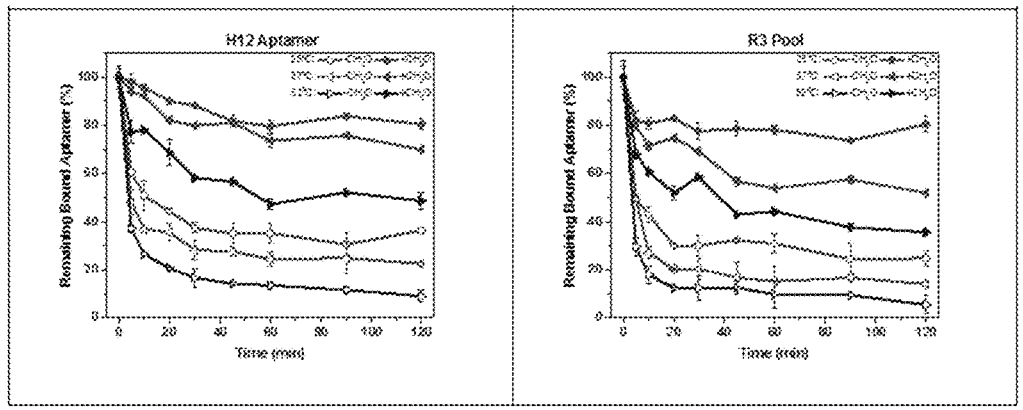
FIG. 4B Dissociation of round 3 pool against HER2.
Figure 4C:
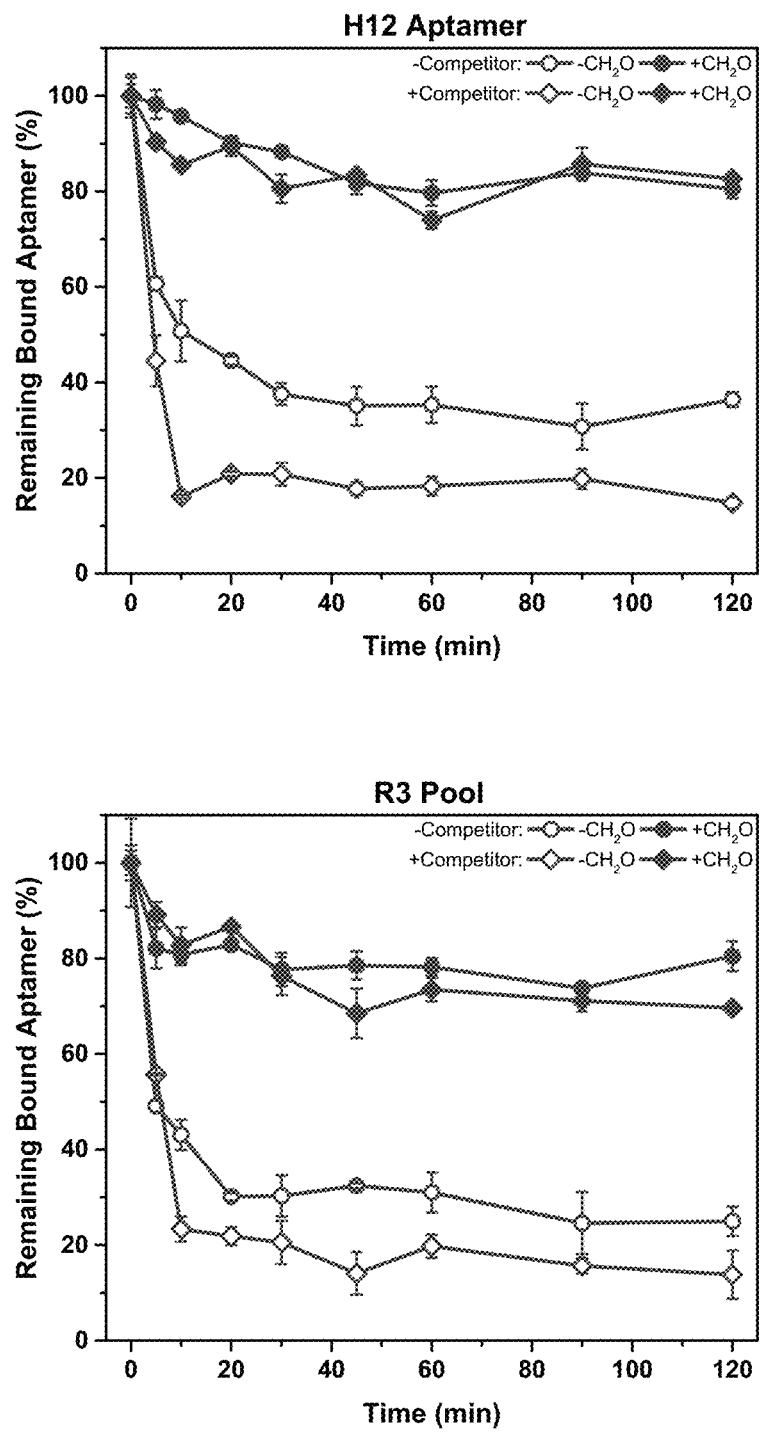
FIG. 4C Dissociation of round 3 pool against HER2.

To further investigate the dissociation of HER2-aptamer complexes, the complexes were diluted in different buffer or temperature to break the equilibrium and investigate the stability of complexes with or without formaldehyde cross-linking. A ratio comparing the amount of bound aptamer before dilution with the remaining amount of bound aptamer after dilution as a function of time was determined. Firstly, the complexes of H12 aptamer and HER2 protein, with or without formaldehyde cross-linking, were diluted and incubated in different buffer over 120-min period (FIG. 4A). The cross-linked complexes resulted in low dissociation in binding buffer (over 80%). Surprisingly, more than 70% of complexes remained in denature condition (urea washing buffer and pure water). Without formaldehyde cross-linking, the complexes, even in binding buffer, displayed fast dissociation and resulted in around 35% of complexes remaining. In urea washing buffer, more than 90% of complexes dissociated after 120-min incubation. Secondly, increasing incubation temperature can accelerate the dissociation of the complexes with or without formaldehyde cross-linking (FIG. 4B). The final ratios of bound aptamer were 36%, 22% and 9% when the complexes were incubated for 2 hours at 25° C., 37° C. and 52° C., respectively. Although cross-linked complexes showed slight desorption at 37° C. incubation, the percentage of bound aptamer dropped from 80% to 50% when the incubation temperature raised from 25° C. to 52° C. Because formaldehyde cross-linking is reversible at high temperature, increasing temperature can cause the break of covalent bond and desorption of complexes. Thirdly, competition experiments were preformed by adding excess unlabeled H12 aptamer (1 µM, 40×) into pre-formed complexes (FIG. 4C). Whereas addition of unlabeled H12 aptamer as competitor resulted in negligible dissociation of cross-linked complexes, dissociation of complexes without formaldehyde cross-linking was observed in presence of unlabeled H12 aptamer. The percentage of bound aptamer dropped from 35% to 15%. As shown in FIG. 4 D-F, round 3 pool displayed similar dissociation pattern to H12 aptamer at different buffer and different temperature. Due to the mixture of sequences with different affinity, ratio of bound aptamer of round 3 pool after 2-hour period is slightly lower than that of H12 aptamer. From the above results, formaldehyde cross-linking is proved to be an effective method to prevent the dissociation of protein-aptamer complexes.

Formaldehyde Cross-Linking can Retain the Selectivity of Aptamer

Figure 5A:
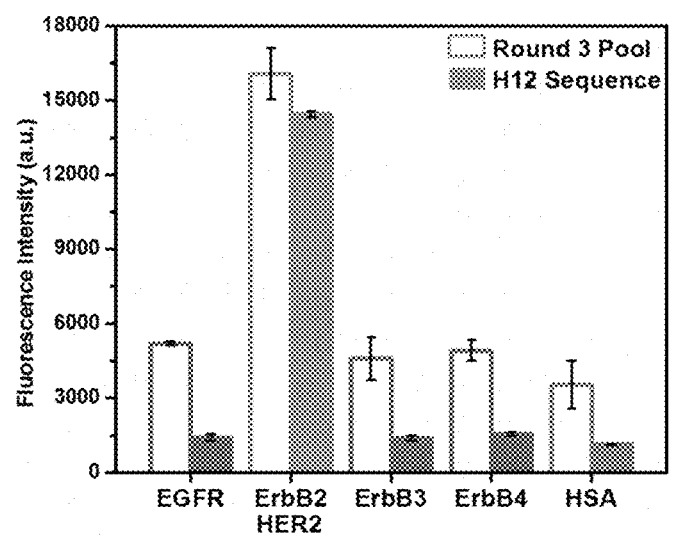
FIG. 5A Selective binding of Round 3 enriched ssDNA pool and H12 (SEQ ID NO: 13) aptamer to EGFR family proteins. FAM-labeled round 3 pool against HER2 or H12 aptamer (10 nM) were incubated with magnetic beads ($10^7$ beads) coated with EGFR, HER2, ErbB3, ErbB4 or HSA, respectively. The fluorescence intensity of bound ssDNA was measured by a fluorescence plate reader after washing and releasing.

The specificity of the HER2 aptamer was investigated by determining its binding with other proteins from the EGFR family, such as EGFR, HER3 and HER4. After incubation with magnetic beads coated with the four EGFR family proteins, the fluorescence signal of H12 bound on the HER2 protein was more than 10-fold higher than the other EGFR family proteins (FIG. 5A). This result proved that the H12 aptamer was specifically bound with the HER2 protein. In contrast, the ssDNA pool of round 3 displayed only about 4 times higher binding with the HER2 protein than the other EGFR family proteins. This was because many sequences other than H12 were included in the round 3 pool which may have resulted in cross reactivity or non-specific binding with other proteins.

Figure 5B:
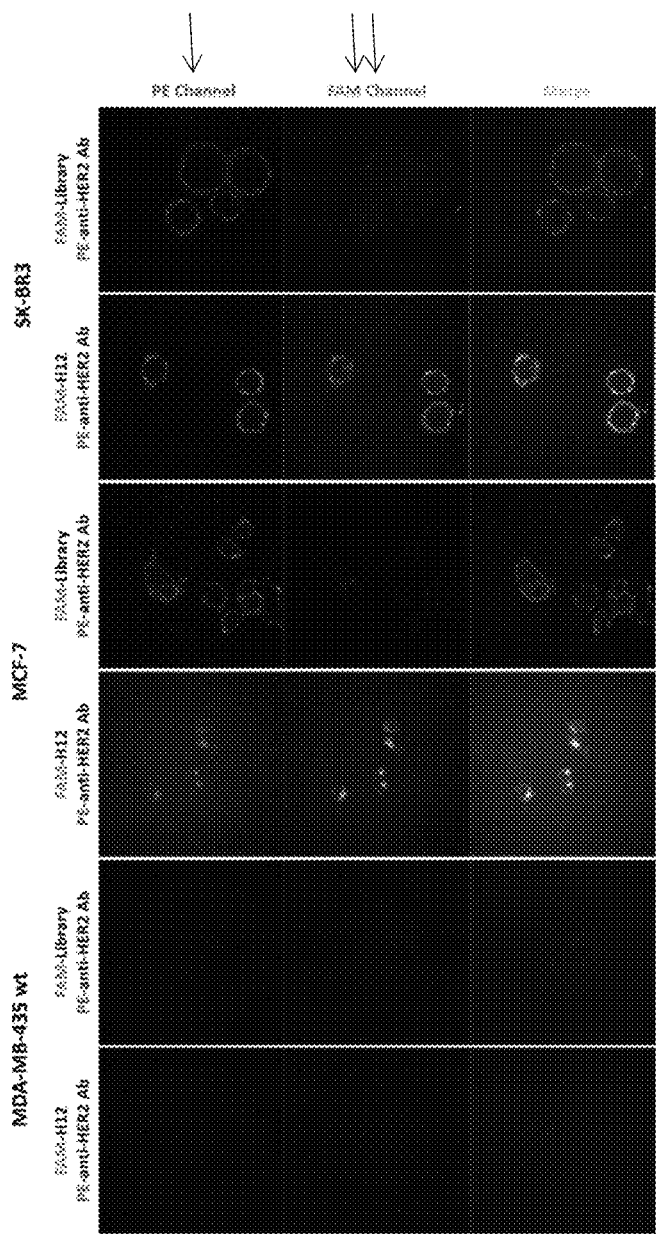
FIG. 5B Fluorescence confocal images of cultured SK-BR3, MCF-7 and MDA-MB-435 wt cells stained with FAM-labeled library or H12 aptamer. PE-labeled anti-human ErbB2/HER2 monoclonal antibody was co-incubated as positive control. First column is PE channel (denoted by single arrow), second column is FAM channel (denoted by double arrow) and third column is the merge of the two channel. The first two rows were SK-BR3 cells, middle two rows were MCF-7 cells, and last two rows were MDA-MB-435 wt cells. Cells in row 1, 3 and 5 were co-incubated with FAM-labeled library and PE-labeled anti-HER2 antibody, and cells in 2, 4, and 6 were co-incubated with FAM-labeled H12 aptamer and PE-labeled anti-HER2 antibody. The final concentration of FAM-labeled library or H12 was 50 nM, and PE-labeled anti-HER2 antibody was 1/50 dilution.

The specific binding of a selected aptamer to HER2 protein expressed on the surface of cancer cells was further demonstrated by confocal imaging. SK-BR3 and MCF-7 are HER2 overexpressed cell lines and MDA-MB-435 wt is a HER2-negative cell line. After incubating these cells with fluorescently labeled aptamers and antibodies, namely FAM-labeled HER2 aptamer and PE-labeled anti-H ER2 antibody, both SK-BR3 and MCF-7 cells displayed green fluorescence from FAM and red fluorescence from PE, but no obvious fluorescence signal was observed from MDA-MB-435 wt (as shown in FIG. 5B). Fluorescence from FAM and PE channels were highly co-localized in SK-BR3 and MCF-7 cells. This represents the co-binding of HER2 aptamer and anti-HER2 antibody on the HER2 protein expressed on the surface of cells. In contrast, none of these three cell lines displayed any significant green fluorescence after incubating with FAM-labeled unselected library. It also resulted in the loss of co-localization of fluorescence from FAM and PE channels. These results further confirmed that the HER2 aptamer selectively recognize HER2 protein on the surface of cancer cells. This implies that HER2 aptamers would be reliable affinity probes for cancer cell analysis to differentiate HER2-positive cells from negative cells. The formaldehyde cross-linking retains the selectivity of aptamer against his target.

Discussion

In this work, we demonstrate an improved SELEX process combined with formaldehyde induced cross-linking that accelerates the discovery of aptamers with high binding affinity and low rates of dissociation. Formaldehyde is a highly reactive reagent that produces cross-links in both protein-protein and protein-DNA or -RNA interactions under physiological conditions. Formaldehyde can only form cross-links between any two reactive groups that are in close proximity, because formaldehyde-mediated cross-linking forms very short bridges (only 2A) (21). Only two reactive groups in very close contact can be joined together by formaldehyde. Also, the Schiff-base intermediate is highly reactive and easily dehydrated. Due to these reasons, formaldehyde mediated cross-linking between protein and DNA is based on the physiological DNA-protein interaction. This means that the target protein and the aptamer candidate should first form a complex, which brings reactive groups from protein or DNA in very close contact. Then, formaldehyde forms cross-links specifically between the target protein and the aptamer candidate within the complex (FIG. 1B and FIG. 5A). Also, formaldehyde cross-linking retains the binding of the aptamer to the protein in a concentration dependent manner (FIG. 1B). Furthermore, cross-linking could not be generated between unbound DNA and protein, such as aptamer 20t with HSA protein or a random DNA library with PDGF-BB protein (FIG. 1B and 1C). Through SELEX with formaldehyde cross-linking, the aptamer H12 displays high selectivity to HER2 protein (FIG. 5A). Another important point is that formaldehyde-based cross-linking is fully reversible at high temperatures (>60° C.) in aqueous solution. These two features make the application of formaldehyde cross-linking feasible in the SELEX process.

Figure 6:
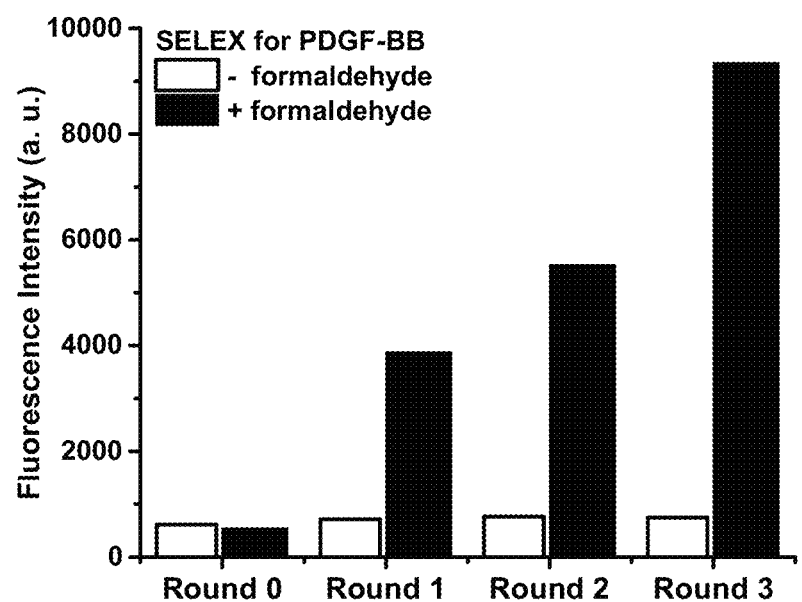
FIG. 6 Evolution process of SELEX for PDGF-BB protein under the condition with or without formaldehyde cross-linking. FAM-labeled ssDNA pools (5 nM) from each round of selection were incubated with PDGF-BB coated magnetic beads ($10^7$ beads). The fluorescence intensity of bound ssDNA was measured by plate reader after washing and releasing.

The conventional SELEX process relies on the formation of target-aptamer complexes by affinity binding which is dynamic and non-covalent. However, the affinity binding is not always sufficient for generation of aptamers with high affinity against many proteins. To compromise, mild partition conditions are always applied to prevent the loss of bound candidates. With conventional SELEX for HER2 and PDGF-BB protein, the enriched ssDNA pool displayed no improvement of binding affinity after three rounds (FIG. 2A and FIG. 6). By this method, the non-specific or low-affinity DNA cannot be effectively eliminated and usually dominated the ssDNA pool in early rounds. According to a previous report, the high binding affinity aptamers against PDGF-BB protein were selected after 15 rounds of selection (40). More rounds of selection are required to obtain the enriched high-affinity pool, however increasing the rounds of selection may introduce PCR biases and artifacts (9, 10). Formaldehyde cross-linking can overcome this limitation by stabilizing the complexes with the formation of cross-links between target proteins and aptamers. Cross-linking converts dynamic, non-covalent interactions between protein and DNA into stable, covalent bonds, which prevents the dissociation of complexes during the following partition step. Although the target protein may denature in stringent conditions (such as urea buffer), the bound DNA are covalently cross-linked with protein and are not washed away. From the dissociation experiments (FIG. 4A, FIG. 4B, FIG. 4C), the cross-linked complexes demonstrated higher stability than that of non-covalent complexes. The aptamer sequences may be lost during the partition step without the formaldehyde cross-linking. The high-affinity sequences are greatly enriched only in three rounds of formaldehyde cross-linking modified SELEX. Compared with the initial ssDNA library, the relative binding of enriched pool for HER2 and PDGF-BB protein increased about 7-fold after only single round of SELEX (FIG. 1B). Combined with formaldehyde cross-linking, stringent wash conditions can eliminate the non-specific and low-affinity binders without interrupting the specific binding. The efficiency of selection is significantly improved and the sequences of aptamer candidates are converged earlier in the enriched pool. In CE-SELEX, a high affinity aptamer pool was obtained with one or four rounds of selection, but none of the sequences that displayed homology was identified (42-44). Through SELEX with formaldehyde cross-linking for HER2 protein, there were 6 aptamer sequences found that repeated, out of the total 53 correct insert sequences. Surprisingly, the H12 sequence repeated 11 times. The H12 sequence displayed high affinity to the HER2 protein with a $K_d$ of 6.4±2.7 nM. The $K_d$ of H12 was similar to the bulk $K_d$ of round 3 pool. H12 was the dominating sequence in the enriched pool after round 3. The enrichment of high-affinity aptamers is greatly enhanced during the modified SELEX process when combined with formaldehyde cross-linking. Without the interference of undesired background sequences, the sequences of binding aptamers are converged in earlier rounds of selection.

Surprisingly, the H12 aptamer generated from formaldehyde cross-linking modified SELEX displayed similar binding affinity with or without formaldehyde (FIG. 3B). The aptamer H12 can form stable and cross-linked complexes with HER2, but H12 also can specifically bind to HER2 protein without formaldehyde at high affinity. When aptamer H12 binds to its target HER2, it involves two events: affinity binding and cross-linking. First, H12 forms complexes with HER2, then H12-HER2 complexes are cross-linked by formaldehyde. The formation of the complexes brings H12 and HER2 close to each other. The contact sites of both H12 and HER2 sequences contains amino or other reactive groups that are available for cross-linking. Formaldehyde enters the contact site within the complexes and joins two amino or other reactive groups that are in close proximity together. The affinity binding of the aptamer to HER2 protein is required for the formation of cross-links. Even without formaldehyde cross-linking, aptamer H12 can still specifically bind to HER2 proteins with high affinity. Some sequences in enriched ssDNA pool of third round are low affinity to HER2 protein. The complexes will dissociate during the washing step without formaldehyde cross-linking. Formation of cross-linked complexes between HER2 and the low affinity aptamer will increase apparent affinity and statured fluorescence intensity. Aptamer H12 possesses high affinity to HER2 for binding and reactive groups at optimal positions for cross-linking. Further studies are needed to characterize the structure of formaldehyde-induced cross-links between HER2 and aptamer H12.

Formaldehyde cross-linking can also improve the further application of aptamer in clinical diagnostics (0-23). Potential protein biomarkers for disease often present in serum or plasma in the nM range of concentrations and accompanied with a high abundance of proteins (45). The detection of a particular target protein depends critically on not only increasing signal from target detection, but also decreasing noise from background signals. High signals result from the low dissociation of cross-linked complexes of target protein and aptamer. Low background can be achieved by effectively removing proteins nonspecifically bound to the surface of supporting matrix. After forming covalently bound complexes, the supporting matrix can be washed under the harshest conditions, such as using detergents, using high salt concentrations or even denaturation. Therefore, highly sensitive assays can be used because of the high signal-to-noise ratio. Photoaptamer can also form covalent bond between protein target and aptamer. However, incorporating modified nucleotid, such as bromodeoxyuridine, into photoaptamer, to some extent, increase the difficulty of SELEX and restrict the potential application of photoaptamer. Additionally, an extra source of radiation is needed to induce the photocrosslinking. In contrast to photoaptamers, the generation of cross-linking by formaldehyde is much simpler. It requires only the additional step of adding formaldehyde into preformed target-aptamer complexes in the procedure of both SELEX and detection. The aptamers with four natural nucleotides can directly form cross-links with the target protein by formaldehyde under the physiological conditions.

REFERENCES

Tuerk C & Gold L (1990) Systematic evolution of ligands by exponential enrichment: RNA ligands to bacteriophage T4 DNA polymerase. Science 249(4968): 505-510.

Ellington AD & Szostak J W (1990) INVITRO SELECTION OF RNA MOLECULES THAT BIND SPECIFIC LIGANDS. Nature 346(6287): 818-822.

Li F, et al. (2015) Aptamers facilitating amplified detection of biomolecules. Analytical chemistry 87(1): 274-292.

Keefe AD, Pai S, & Ellington A (2010) Aptamers as therapeutics. Nature reviews. Drug discovery 9(7): 537-550.

Tan W, Donovan M J, & Jiang J (2013) Aptamers from cell-based selection for bioanalytical applications. Chemical reviews 113(4): 2842-2862.

Stoltenburg R, Reinemann C, & Strehlitz B (2007) SELEX a (r)evolutionary method to generate high-affinity nucleic acid ligands. Biomol Eng 24(4): 381-403.

Gopinath S C B (2007) Methods developed for SELEX. Analytical and Bioanalytical Chemistry 387(1): 171-182.

Aquino-Jarquin G & Toscano-Garibay J D (2011) RNA Aptamer Evolution: Two Decades of SELEction. International journal of molecular sciences 12(12): 9155-9171.

Cho M, et al. (2010) Quantitative selection of DNA aptamers through microfluidic selection and high-throughput sequencing. Proc Natl Acad Sci U S A 107(35): 15373-15378.

Schutze T, et al. (2011) Probing the SELEX process with next-generation sequencing. PloS one 6(12): e29604.

Gold L, et al. (2010) Aptamer-based multiplexed proteomic technology for biomarker discovery. PloS one 5(12): e15004.

Vaught J D, et al. (2010) Expanding the chemistry of DNA for in vitro selection. J Am Chem Soc 132(12): 4141-4151.

Shoji A, Kuwahara M, Ozaki H, & Sawai H (2007) Modified DNA aptamer that binds the (R)-isomer of a thalidomide derivative with high enantioselectivity. J Am Chem Soc 129(5): 1456-1464.

Kimoto M, Yamashige R, Matsunaga K, Yokoyama S, & Hirao I (2013) Generation of high-affinity DNA aptamers using an expanded genetic alphabet. Nature biotechnology 31(5): 453-457.

Sefah K, et al. (2014) In vitro selection with artificial expanded genetic information systems. Proceedings of the National Academy of Sciences of the United States of America 111(4): 1449-1454.

Gelinas A D, et al. (2014) Crystal structure of interleukin-6 in complex with a modified nucleic acid ligand. The Journal of biological chemistry 289(12): 8720-8734.

Jensen K B, Atkinson B L, Willis M C, Koch T H, & Gold L (1995) Using in vitro selection to direct the covalent attachment of human immunodeficiency virus type 1 Rev protein to high-affinity RNA ligands. Proc. Natl. Acad. Sci. U. S. A. 92(26): 12220-12224.

Golden M C, Collins B D, Willis M C, & Koch T H (2000) Diagnostic potential of PhotoSELEX-evolved ssDNA aptamers. J Biotechnol 81(2-3): 167-178.

Bock C, et al. (2004) Photoaptamer arrays applied to multiplexed proteomic analysis. Proteomics 4(3): 609-618.

Smith D (2002) Sensitivity and Specificity of Photoaptamer Probes. Molecular & Cellular Proteomics 2(1): 11-18.

Gander T R & Brody E N (2005) Photoaptamer chips for clinical diagnostics. Expert review of molecular diagnostics 5(1): 1-3.

Sprung M M (1940) A summary of the reactions of aldehydes with amines. Chem Rev 26(3): 297-338.

Kunkel G R, Mehrabian M, & Martinson H G (1981) Contact-site cross-linking agents. Molecular and cellular biochemistry 34(1): 3-13.

Metz B, et al. (2004) Identification of formaldehyde-induced modifications in proteins: reactions with model peptides. The Journal of biological chemistry 279(8): 6235-6243.

Berg D, Malinowsky K, Reischauer B, Wolff C, & Becker KF (2011) Use of Formalin-Fixed and Paraffin-Embedded Tissues for Diagnosis and Therapy in Routine Clinical Settings. Methods Mol Biol 785: 109-122.

Jackson V (1978) Studies on Histone Organization in Nucleosome Using Formaldehyde as a Reversible Cross-Linking Agent. Cell 15(3): 945-954.

Orlando V (2000) Mapping chromosomal proteins in vivo by formaldehyde-crosslinked-chromatin immunoprecipitation. Trends in biochemical sciences 25(3): 99-104.

Dahl J A & Collas P (2008) MicroChiP—a rapid micro chromatin immunoprecipitation assay for small cell samples and biopsies. Nucleic acids research 36(3): e15.

Klockenbusch C, O'Hara J E, & Kast J (2012) Advancing formaldehyde cross-linking towards quantitative proteomic applications. Anal Bioanal Chem 404(4): 1057-1067.

Sutherland B W, Toews J, & Kast J (2008) Utility of formaldehyde cross-linking and mass spectrometry in the study of protein-protein interactions. Journal of mass spectrometry: JMS 43(6): 699-715.

Qin H & Wang Y (2009) Exploring DNA-binding proteins with in vivo chemical cross-linking and mass spectrometry. Journal of proteome research 8(4): 1983-1991.

Mcghee J D & Hippel P H V (1975) Formaldehyde as a Probe of DNA Structure. 1. Reaction with Exocyclic Amino-Groups of DNA Bases. Biochemistry-Us 14(6): 1281-1296.

Mcghee J D & Hippel P H V (1975) Formaldehyde as a Probe of DNA Structure. 2. Reaction with Endocyclic Imino Groups of DNA Bases. Biochemistry-Us 14(6): 1297-1303.

Barker S, Weinfeld M, & Murray D (2005) DNA-protein crosslinks: their induction, repair, and biological consequences. Mutation research 589(2): 111-135.

Lu K, et al. (2010) Structural characterization of formaldehyde-induced cross-links between amino acids and deoxynucleosides and their oligomers. J Am Chem Soc 132(10): 3388-3399.

Solomon M J & Varshaysky A (1985) Formaldehyde-mediated DNA-protein crosslinking: a probe for in vivo chromatin structures. Proc Natl Acad Sci U S A 82(19): 6470-6474.

Rubin I & Yarden Y (2001) The basic biology of HER2. Annals of oncology: official journal of the European Society for Medical Oncology/ESMO 12 Suppl 1: S3-8.

Moasser M M (2007) Targeting the function of the HER2 oncogene in human cancer therapeutics. Oncogene 26(46): 6577-6592.

Tebbutt N, Pedersen M W, & Johns T G (2013) Targeting the ERBB family in cancer: couples therapy. Nature reviews. Cancer 13(9): 663-673.

Green L S, et al. (1996) Inhibitory DNA ligands to platelet-derived growth factor B-chain. Biochemistry-Us 35(45): 14413-14424.

Wiegand T W, et al. (1996) High-affinity oligonucleotide ligands to human IgE inhibit binding to Fc epsilon receptor I. J Immunol 157(1): 221-230.

Mendonsa S D & Bowser M T (2004) In vitro evolution of functional DNA using capillary electrophoresis. J Am Chem Soc 126(1): 20-21.

Berezovski M, et al. (2005) Nonequilibrium capillary electrophoresis of equilibrium mixtures: a universal tool for development of aptamers. J Am Chem Soc 127(9): 3165-3171.

Berezovski M, Musheev M, Drabovich A, & Krylov S N (2006) Non-SELEX selection of aptamers. J Am Chem Soc 128(5): 1410-1411.

Ludwig J A & Weinstein J N (2005) Biomarkers in cancer staging, prognosis and treatment selection. Nature reviews. Cancer 5(11): 845-856.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A method for producing a nucleic acid aptamer, comprising: (a) a complex formation step of mixing a single-stranded nucleic acid library with a target substance in a solution to form a complex of a single-stranded nucleic acid and the target substance; (b) a crosslinking step of mixing a crosslinking agent with the complex of a single-stranded nucleic acid and the target substance from step (a), (c) a recovery step of recovering the complex from the solution; (d) an amplification step of recovering the single-stranded nucleic acid from the complex and then amplifying the single-stranded nucleic acid by a nucleic acid amplification method; (e) and a single-stranded nucleic acid preparation step of converting the double-stranded nucleic acids obtained in the amplification step into single strands wherein the target is a peptide.

2. The method of claim 1, wherein the target substance is coated on a solid-phase support to immobilize the complex onto the solid-phase support.

3. The method of claim 2, wherein the solid-phase support comprises a magnetic bead.

4. The method of claim 1, further comprising a repetitive step of repeating several times the round from the complex formation step to the single-stranded nucleic acid preparation step using the single-stranded nucleic acids obtained in the single-stranded nucleic acid preparation step as a new single-stranded nucleic acid library.

5. The method of claim 4, wherein the repetitive step involves repeating 2 to 15 times the round from the complex formation step to the single-stranded nucleic acid preparation step.

6. The method of claim 1, wherein the nucleic acid is a DNA.

7. The method of claim 6, wherein the DNA comprises non-modified nucleotides.

8. The method of claim 1, wherein the peptide is human epidermal growth factor receptor 2 (ErbB2/HER2), human platelet-derived growth factor-BB (PDGF-BB), human immunoglobulin E (IgE), ubiquitin, cytotoxic T-lymphocyte-associated protein 4 (CTLA-4), or programmed death-ligand 1 (PD-L1).

9. The method of claim 1, wherein the target is human epidermal growth factor receptor 2 (ErbB2/HER2) protein (HER2).

10. The method of claim 1, wherein the cross-linking agent is formaldehyde, or paraformaldehyde, or a carbonyl, preferably an aldehyde, preferably an aldehyde that is water soluble.

11. The method of claim 10, wherein said aldehyde includes protected aldehydes, and aldehyde precursors (such as acetals, animals, hemiaminals, urotropine, formaldehyde-releasing compounds).

12. The method of claim 10, wherein said carbonyl includes aldehydes, ketones and keto esters with reactive carbonyl groups.

13. The method of claim 1, wherein said cross-linking agent is an organic compound which contain at least one aldehyde group therein capable of reacting with amine groups which includes but are not limited to for example, formaldehyde, acetaldehyde, propionaldehyde, isobutyraldehyde, chloral, hydroxyethylaldehyde, hydroxypivalaldehyde, acrolein, crotonaldehyde, glycolaldehyde, glycoxylic acid, furfural, hydroxymethylfurfural, glucose, salicylaldehyde, hydroxyacetaldehyde, glyceraldehyde and the like, or polyaldehydes i.e. known organic compounds having more than one aldehyde group therein, such as glyoxal, methylglyoxal, glutaraldehyde, paraformaldehyde and the like, and all the commercial derivatives thereof sold in the form of various condensates.

* * * * *

SEQUENCE LISTING

```
<160> NUMBER OF SEQ ID NOS: 58

<210> SEQ ID NO 1
<211> LENGTH: 40
<212> TYPE: DNA
<213> ORGANISM: Artificial Sequence
<220> FEATURE:
<223> OTHER INFORMATION: aptamer

<400> SEQUENCE: 1 tgccoctagg cgtggctgca gcgtctaatt gtgtttatga                              40

<210> SEQ ID NO 2
<211> LENGTH: 40
<212> TYPE: DNA
<213> ORGANISM: artificial
<220> FEATURE:
<223> OTHER INFORMATION: aptamer

<400> SEQUENCE: 2
attgggtcta tgggttgaat catttcggac gttttacgta                              40

<210> SEQ ID NO 3
<211> LENGTH: 40
<212> TYPE: DNA
<213> ORGANISM: artificial
<220> FEATURE:
<223> OTHER INFORMATION: aptamer

<400> SEQUENCE: 3
cgacatgtgc tgcgtgtacg actgtgtgct ctatctcgag                              40

<210> SEQ ID NO 4
<211> LENGTH: 40
<212> TYPE: DNA
<213> ORGANISM: artificial
<220> FEATURE:
<223> OTHER INFORMATION: aptamer

<400> SEQUENCE: 4
ctacgcaaca atcataggtg ataccgggct gttgtacaat                              40

<210> SEQ ID NO 5
<211> LENGTH: 40
<212> TYPE: DNA
<213> ORGANISM: artificial
<220> FEATURE:
<223> OTHER INFORMATION: aptamer

<400> SEQUENCE: 5
gtagggatcg ctagaagggt caaagttagg tcatgtaggg                              40

<210> SEQ ID NO 6
<211> LENGTH: 40
<212> TYPE: DNA
```

```
<213> ORGANISM: artificial
<220> FEATURE:
<223> OTHER INFORMATION: aptamer

<400> SEQUENCE: 6
aaccgtaggt gaaacggaag tcccggttgg ggatcaatat                    40

<210> SEQ ID NO 7
<211> LENGTH: 40
<212> TYPE: DNA
<213> ORGANISM: artificial
<220> FEATURE:
<223> OTHER INFORMATION: aptamer

<400> SEQUENCE: 7
aaccttagta ggtactcatg acgtggtcca agccttgttt                    40

<210> SEQ ID NO 8
<211> LENGTH: 40
<212> TYPE: DNA
<213> ORGANISM: artificial
<220> FEATURE:
<223> OTHER INFORMATION: aptamer

<400> SEQUENCE: 8
gagggggggc cgctactgag cactcaaaga cgcaatgccc                    40

<210> SEQ ID NO 9
<211> LENGTH: 40
<212> TYPE: DNA
<213> ORGANISM: artificial
<220> FEATURE:
<223> OTHER INFORMATION: aptamer

<400> SEQUENCE: 9
gtgtgcagca acgagactca gcgactagcc cgtacgcctg                    40

<210> SEQ ID NO 10
<211> LENGTH: 40
<212> TYPE: DNA
<213> ORGANISM: artificial
<220> FEATURE:
<223> OTHER INFORMATION: aptamer

<400> SEQUENCE: 10
tggagtgatt gctctagtag ggtttcatgg ggcccgatcc                    40

<210> SEQ ID NO 11
<211> LENGTH: 40
<212> TYPE: DNA
<213> ORGANISM: artificial
<220> FEATURE:
<223> OTHER INFORMATION: aptamer

<400> SEQUENCE: 11
tggagtgatt gctctagtag ggtttcatgg ggcccgatcc                    40

<210> SEQ ID NO 12
<211> LENGTH: 40
<212> TYPE: DNA
<213> ORGANISM: artificial
<220> FEATURE:
<223> OTHER INFORMATION: aptamer

<400> SEQUENCE: 12
tggagtgatt gctctagtag ggtttcatgg ggcccgatcc                    40
```

<210> SEQ ID NO 13
<211> LENGTH: 40
<212> TYPE: DNA
<213> ORGANISM: artificial
<220> FEATURE:
<223> OTHER INFORMATION: aptamer

<400> SEQUENCE: 13
ggcgcttaca cgcaggttga ctcagactag actctacagc                               40

<210> SEQ ID NO 14
<211> LENGTH: 40
<212> TYPE: DNA
<213> ORGANISM: artificial
<220> FEATURE:
<223> OTHER INFORMATION: aptamer

<400> SEQUENCE: 14
ggcgcttaca cgcaggttga ctcagactag actctacagc                               40

<210> SEQ ID NO 15
<211> LENGTH: 40
<212> TYPE: DNA
<213> ORGANISM: artificial
<220> FEATURE:
<223> OTHER INFORMATION: aptamer

<400> SEQUENCE: 15
ggcgcttaca cgcaggttga ctcagactag actctacagc                               40

<210> SEQ ID NO 16
<211> LENGTH: 40
<212> TYPE: DNA
<213> ORGANISM: artificial
<220> FEATURE:
<223> OTHER INFORMATION: aptamer

<400> SEQUENCE: 16
ggcgcttaca cgcaggttga ctcagactag actctacagc                               40

<210> SEQ ID NO 17
<211> LENGTH: 40
<212> TYPE: DNA
<213> ORGANISM: Artificial Sequence
<220> FEATURE:
<223> OTHER INFORMATION: aptamer

<400> SEQUENCE: 17
ggcgcttaca cgcaggttga ctcagactag actctacagc                               40

<210> SEQ ID NO 18
<211> LENGTH: 40
<212> TYPE: DNA
<213> ORGANISM: artificial sequence
<220> FEATURE:
<223> OTHER INFORMATION: aptamer

<400> SEQUENCE: 18
ggcgcttaca cgcaggttga ctcagactag actctacagc                               40

<210> SEQ ID NO 19
<211> LENGTH: 40
<212> TYPE: DNA
<213> ORGANISM: artificial sequence
<220> FEATURE:

<223> OTHER INFORMATION: aptamer

<400> SEQUENCE: 19
ggcgcttaca cgcaggttga ctcagactag actctacagc        40

<210> SEQ ID NO 20
<211> LENGTH: 40
<212> TYPE: DNA
<213> ORGANISM: artificial sequence
<220> FEATURE:
<223> OTHER INFORMATION: aptamer

<400> SEQUENCE: 20
ggcgcttaca cgcaggttga ctcagactag actctacagc        40

<210> SEQ ID NO 21
<211> LENGTH: 40
<212> TYPE: DNA
<213> ORGANISM: artificial sequence
<220> FEATURE:
<223> OTHER INFORMATION: aptamer

<400> SEQUENCE: 21
ggcgcttaca cgcaggttga ctcagactag actctacagc        40

<210> SEQ ID NO 22
<211> LENGTH: 40
<212> TYPE: DNA
<213> ORGANISM: artificial sequence
<220> FEATURE:
<223> OTHER INFORMATION: aptamer

<400> SEQUENCE: 22
ggcgcttaca cgcaggttga ctcagactag actctacagc        40

<210> SEQ ID NO 23
<211> LENGTH: 40
<212> TYPE: DNA
<213> ORGANISM: artificial sequence
<220> FEATURE:
<223> OTHER INFORMATION: aptamer

<400> SEQUENCE: 23
ggcgcttaca cgcaggttga ctcagactag actctacagc        40

<210> SEQ ID NO 24
<211> LENGTH: 40
<212> TYPE: DNA
<213> ORGANISM: artificial sequence
<220> FEATURE:
<223> OTHER INFORMATION: aptamer

<400> SEQUENCE: 24
gattggcagt tagcgttttt ctgagcattc gaaggttata        40

<210> SEQ ID NO 25
<211> LENGTH: 40
<212> TYPE: DNA
<213> ORGANISM: artificial sequence
<220> FEATURE:
<223> OTHER INFORMATION: aptamer

<400> SEQUENCE: 25
gattggcagt tagcgttttt ctgagcattc gaaggttata        40

<210> SEQ ID NO 26
<211> LENGTH: 40
<212> TYPE: DNA
<213> ORGANISM: artificial sequence
<220> FEATURE:
<223> OTHER INFORMATION: aptamer

<400> SEQUENCE: 26
gaatccttca ctggtgggtt ctgtttcggc tttttaaaat        40

<210> SEQ ID NO 27
<211> LENGTH: 40
<212> TYPE: DNA
<213> ORGANISM: artificial sequence
<220> FEATURE:
<223> OTHER INFORMATION: aptamer

<400> SEQUENCE: 27
gaatccttca ctggtgggtt ctgtttcggc tttttaaaat        40

<210> SEQ ID NO 28
<211> LENGTH: 40
<212> TYPE: DNA
<213> ORGANISM: artificial sequence
<220> FEATURE:
<223> OTHER INFORMATION: aptamer

<400> SEQUENCE: 28
gaatccttca ctggtgggtt ctgtttcggc tttttaaaat        40

<210> SEQ ID NO 29
<211> LENGTH: 40
<212> TYPE: DNA
<213> ORGANISM: artificial sequence
<220> FEATURE:
<223> OTHER INFORMATION: aptamer

<400> SEQUENCE: 29
gaatccttca ctggtgggtt ctgtttcggc tttttaaaat        40

<210> SEQ ID NO 30
<211> LENGTH: 40
<212> TYPE: DNA
<213> ORGANISM: artificial sequence
<220> FEATURE:
<223> OTHER INFORMATION: aptamer

<400> SEQUENCE: 30
catgcggtac cggtgaaact agaacgaatt taaaggcgac        40

<210> SEQ ID NO 31
<211> LENGTH: 40
<212> TYPE: DNA
<213> ORGANISM: artificial sequence
<220> FEATURE:
<223> OTHER INFORMATION: aptamer

<400> SEQUENCE: 31
catgcggtac cggtgaaact agaacgaatt taaaggcgac        40

<210> SEQ ID NO 32
<211> LENGTH: 40
<212> TYPE: DNA
<213> ORGANISM: artificial sequence
<220> FEATURE:
<223> OTHER INFORMATION: aptamer

<400> SEQUENCE: 32
catgcggtac cggtgaaact agaacgaatt taaaggcgac                                40

<210> SEQ ID NO 33
<211> LENGTH: 40
<212> TYPE: DNA
<213> ORGANISM: artificial sequence
<220> FEATURE:
<223> OTHER INFORMATION: aptamer

<400> SEQUENCE: 33
ccttaggcta gggcaatttc aactcgcttg acgtcgaata                                40

<210> SEQ ID NO 34
<211> LENGTH: 40
<212> TYPE: DNA
<213> ORGANISM: artificial sequence
<220> FEATURE:
<223> OTHER INFORMATION: aptamer

<400> SEQUENCE: 34
ccttaggcta gggcaatttc aactcgcttg acgtcgaata                                40

<210> SEQ ID NO 35
<211> LENGTH: 40
<212> TYPE: DNA
<213> ORGANISM: artificial sequence
<220> FEATURE:
<223> OTHER INFORMATION: aptamer

<400> SEQUENCE: 35
ttgagtcatt accgtaagta catcaactac ttagttagtc                                40

<210> SEQ ID NO 36
<211> LENGTH: 40
<212> TYPE: DNA
<213> ORGANISM: artificial sequence
<220> FEATURE:
<223> OTHER INFORMATION: aptamer

<400> SEQUENCE: 36
ttgagtcatt accgtaagta catcaactac ttagttagtc                                40

<210> SEQ ID NO 37
<211> LENGTH: 40
<212> TYPE: DNA
<213> ORGANISM: artificial sequence
<220> FEATURE:
<223> OTHER INFORMATION: aptamer

<400> SEQUENCE: 37
gtcgagagta taatatttcc gcttaaacta gtgtgtcgcc                                40

<210> SEQ ID NO 38
<211> LENGTH: 40
<212> TYPE: DNA
<213> ORGANISM: artificial sequence
<220> FEATURE:
<223> OTHER INFORMATION: aptamer

<400> SEQUENCE: 38
gtcgagagta taatatttcc gcttaaacta gtgtgtcgcc                                40

<210> SEQ ID NO 39
<211> LENGTH: 40

```
<212> TYPE: DNA
<213> ORGANISM: artificial sequence
<220> FEATURE:
<223> OTHER INFORMATION: aptamer

<400> SEQUENCE: 39
accatgaaca gctggcattc catggatcta acgcggaatt                      40

<210> SEQ ID NO 40
<211> LENGTH: 40
<212> TYPE: DNA
<213> ORGANISM: artificial sequence
<220> FEATURE:
<223> OTHER INFORMATION: aptamer

<400> SEQUENCE: 40
caattggcgc ggggattccg caccctcgaa tgttcagggc                      40

<210> SEQ ID NO 41
<211> LENGTH: 40
<212> TYPE: DNA
<213> ORGANISM: artificial sequence
<220> FEATURE:
<223> OTHER INFORMATION: aptamer

<400> SEQUENCE: 41
tgggaagtgt tacaattctg gtaggggtgt ggatttaggg                      40

<210> SEQ ID NO 42
<211> LENGTH: 40
<212> TYPE: DNA
<213> ORGANISM: artificial sequence
<220> FEATURE:
<223> OTHER INFORMATION: aptamer

<400> SEQUENCE: 42
gggcacgcat agcaaggcgt atatgaagcg tcagttttcc                      40

<210> SEQ ID NO 43
<211> LENGTH: 40
<212> TYPE: DNA
<213> ORGANISM: artificial sequence
<220> FEATURE:
<223> OTHER INFORMATION: aptamer

<400> SEQUENCE: 43
ggagttatcc attcgcacat aactgcattc atccgcttag                      40

<210> SEQ ID NO 44
<211> LENGTH: 40
<212> TYPE: DNA
<213> ORGANISM: artificial sequence
<220> FEATURE:
<223> OTHER INFORMATION: aptamer

<400> SEQUENCE: 44
tagtctgatg cgatatactc ggcggtcggg ggggtaggtt                      40

<210> SEQ ID NO 45
<211> LENGTH: 40
<212> TYPE: DNA
<213> ORGANISM: artificial sequence
<220> FEATURE:
<223> OTHER INFORMATION: aptamer

<400> SEQUENCE: 45
```
ggagttttaa gcgtttgtgg cgagataacc tggttgtgca          40

<210> SEQ ID NO 46
<211> LENGTH: 40
<212> TYPE: DNA
<213> ORGANISM: artificial sequence
<220> FEATURE:
<223> OTHER INFORMATION: aptamer

<400> SEQUENCE: 46
cccagatgag gaatgagggc ctcacgtagg gtgtgcagcc          40

<210> SEQ ID NO 47
<211> LENGTH: 40
<212> TYPE: DNA
<213> ORGANISM: artificial sequence
<220> FEATURE:
<223> OTHER INFORMATION: aptamer

<400> SEQUENCE: 47
gcaagacata acgtataatc atggcgatac cctgcttccg          40

<210> SEQ ID NO 48
<211> LENGTH: 40
<212> TYPE: DNA
<213> ORGANISM: artificial sequence
<220> FEATURE:
<223> OTHER INFORMATION: aptamer

<400> SEQUENCE: 48
aactgagtcc atgctactag cagcctgagg tggatactct          40

<210> SEQ ID NO 49
<211> LENGTH: 40
<212> TYPE: DNA
<213> ORGANISM: Artificial Sequence
<220> FEATURE:
<223> OTHER INFORMATION: aptamer

<400> SEQUENCE: 49
gggtatgatt ttggacccga gtaggctatt ttaattcaaa          40

<210> SEQ ID NO 50
<211> LENGTH: 40
<212> TYPE: DNA
<213> ORGANISM: Artificial Sequence
<220> FEATURE:
<223> OTHER INFORMATION: aptamer

<400> SEQUENCE: 50
cagaactgtg acatggcttg gcccatgact taaaggagtg          40

<210> SEQ ID NO 51
<211> LENGTH: 40
<212> TYPE: DNA
<213> ORGANISM: Artificial Sequence
<220> FEATURE:
<223> OTHER INFORMATION: aptamer

<400> SEQUENCE: 51
catatgaacg tttctacaat tttaacgaga cagttttgcg          40

<210> SEQ ID NO 52
<211> LENGTH: 40
<212> TYPE: DNA
<213> ORGANISM: Artificial Sequence

```
<220> FEATURE:
<223> OTHER INFORMATION: aptamer

<400> SEQUENCE: 52
acaattgagg ctatcagttc tgctagaagt tgactggatc                              40

<210> SEQ ID NO 53
<211> LENGTH: 40
<212> TYPE: DNA
<213> ORGANISM: Artificial Sequence
<220> FEATURE:
<223> OTHER INFORMATION: aptamer

<400> SEQUENCE: 53
tctctacctg atgtataatt tacgtcacta agtcccgccg                              40

<210> SEQ ID NO 54
<211> LENGTH: 80
<212> TYPE: DNA
<213> ORGANISM: Artificial Sequence
<220> FEATURE:
<223> OTHER INFORMATION: library
<220> FEATURE:
<221> NAME/KEY: misc_feature
<222> LOCATION: (21)..(60)
<223> OTHER INFORMATION: n is a, c, g, or t

<400> SEQUENCE: 54
agcagcacag aggtcagatg nnnnnnnnnn nnnnnnnnnn nnnnnnnnnn nnnnnnnnnn        60
cctatgcgtg ctaccgtgaa                                                    80

<210> SEQ ID NO 55
<211> LENGTH: 20
<212> TYPE: DNA
<213> ORGANISM: artificial sequence
<220> FEATURE:
<223> OTHER INFORMATION: primer

<400> SEQUENCE: 55
agcagcacag aggtcagatg                                                    20

<210> SEQ ID NO 56
<211> LENGTH: 20
<212> TYPE: DNA
<213> ORGANISM: artificial sequence
<220> FEATURE:
<223> OTHER INFORMATION: primer

<400> SEQUENCE: 56
ttcacggtag cacgcatagg                                                    20

<210> SEQ ID NO 57
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: modified_base
<222> LOCATION: (1)..(1)
<223> OTHER INFORMATION: FAM

<400> SEQUENCE: 57
agcagcacag aggtcagatg                                                    20

<210> SEQ ID NO 58
```

```
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: modified_base
<222> LOCATION: (1)..(1)
<223> OTHER INFORMATION: biotin

<400> SEQUENCE: 58
ttcacggtag cacgcatagg                                              20
```